(12) United States Patent
Jacobsen

(10) Patent No.: US 11,857,127 B2
(45) Date of Patent: Jan. 2, 2024

(54) RAPID TOUCHLESS AUTOMATIC DISPENSING STATION APPARATUS, SYSTEM, AND METHOD

(71) Applicant: Newco Enterprises, Inc., St. Charles, MO (US)

(72) Inventor: Jody G. Jacobsen, Defiance, MO (US)

(73) Assignee: Newco Enterprises, Inc., St. Charles, MO (US)

( * ) Notice: Subject to any disclaimer, the term of this patent is extended or adjusted under 35 U.S.C. 154(b) by 0 days.

(21) Appl. No.: 17/517,193

(22) Filed: Nov. 2, 2021

(65) Prior Publication Data

US 2022/0192436 A1 Jun. 23, 2022

Related U.S. Application Data

(60) Provisional application No. 63/108,708, filed on Nov. 2, 2020.

(51) Int. Cl.
*A47K 5/12* (2006.01)
*A61L 2/00* (2006.01)
*A61L 2/26* (2006.01)

(52) U.S. Cl.
CPC .......... *A47K 5/1217* (2013.01); *A47K 5/1204* (2013.01); *A61L 2/0088* (2013.01);
(Continued)

(58) Field of Classification Search
CPC .... A61L 2/0088; A47K 5/1215; A47K 5/1217
(Continued)

(56) References Cited

U.S. PATENT DOCUMENTS 4,921,150 A * 5/1990 Lagergren ............. G01F 13/006
222/639
4,967,935 A * 11/1990 Celest .................. A47K 5/1217
222/642
(Continued)

FOREIGN PATENT DOCUMENTS

GB 2586090 A * 2/2021 ............... A47K 5/12
WO WO-2012048868 A1 * 4/2012 ........... A41K 5/1215
(Continued)

*Primary Examiner* — Paul R Durand
*Assistant Examiner* — Michael J. Melaragno
(74) *Attorney, Agent, or Firm* — Matthews Edwards LLC

(57) ABSTRACT

A dispensing station apparatus, system, and method for liquid personal hygiene product, including, but not limited to, liquid (including gel) soap, sanitizer, disinfectant and/or cleanser, such as for sanitizing, disinfecting or cleaning one's hands, and, more particularly, that is touchlessly automatically operable to dispense a discrete quantity of the liquid personal hygiene product responsive to sensed presence of a person's hand along a predetermined dispensing path, including rapidly in succession responsive to placement of a succession of hands placed in the path. The apparatus can optionally be modular, to enable configuring to include one or more dispensing stations at multiple positions and heights on a housing of the apparatus, and it can be overall height adjustable, and can include a variety of accessories, including personal protection shielding between the stations, and dispensers for gloves, masks, tissues, etc.

20 Claims, 17 Drawing Sheets

(52) U.S. Cl.
CPC ............. *A61L 2/26* (2013.01); *A61L 2202/14* (2013.01); *A61L 2202/15* (2013.01)

(58) Field of Classification Search
USPC .................................................. 222/63, 214
See application file for complete search history.

(56) References Cited

U.S. PATENT DOCUMENTS

| | | | | |
|---|---|---|---|---|
| 5,105,992 | A * | 4/1992 | Fender | A47K 5/1215 222/325 |
| 5,540,355 | A * | 7/1996 | Hancock | B67D 1/0802 222/64 |
| 6,206,241 | B1 * | 3/2001 | Terrell | A47K 5/1204 222/372 |
| 6,209,752 | B1 * | 4/2001 | Mitchell | A47K 5/1215 222/325 |
| 6,431,400 | B1 * | 8/2002 | O'Maley | B67D 7/344 141/DIG. 1 |
| 7,871,580 | B2 * | 1/2011 | Van Hooser | A61L 2/22 422/292 |
| 9,527,656 | B2 | 12/2016 | Walters et al. | |
| 10,278,549 | B1 * | 5/2019 | Carignan | A47K 5/1217 |
| 11,064,843 | B1 * | 7/2021 | Swartz | E04H 1/1205 |
| 11,129,502 | B1 * | 9/2021 | Jalbert | A47K 5/1217 |
| 11,224,889 | B1 * | 1/2022 | Cadkin | B05B 12/002 |
| 2003/0197026 | A1 * | 10/2003 | Ashe | B65F 1/06 222/174 |
| 2005/0047925 | A1 * | 3/2005 | Davis | F04B 43/1253 417/53 |
| 2008/0099045 | A1 * | 5/2008 | Glenn | G08B 21/245 134/18 |
| 2008/0100441 | A1 * | 5/2008 | Prodanovich | G08B 21/245 340/572.1 |
| 2009/0308887 | A1 * | 12/2009 | Woo | A47K 5/1215 222/113 |
| 2010/0303671 | A1 * | 12/2010 | Bertrand | B05B 12/122 422/119 |
| 2011/0018412 | A1 * | 1/2011 | Swanek | B62B 3/10 312/249.11 |
| 2012/0024890 | A1 * | 2/2012 | Ota | A61L 2/0088 222/608 |
| 2012/0187146 | A1 * | 7/2012 | Chopra | A61L 2/16 222/23 |
| 2012/0248149 | A1 * | 10/2012 | Pelfrey | B05B 9/0872 222/189.1 |
| 2014/0124540 | A1 * | 5/2014 | Ciavarella | B05B 7/0037 222/173 |
| 2014/0172523 | A1 * | 6/2014 | Stob | A47K 5/1217 222/25 |
| 2015/0022361 | A1 * | 1/2015 | Gaisser | G16H 40/20 340/573.1 |
| 2015/0091422 | A1 * | 4/2015 | Adler | A61G 12/001 312/249.11 |
| 2015/0157754 | A1 * | 6/2015 | Rutter | A47K 5/1202 222/52 |
| 2015/0250908 | A1 * | 9/2015 | Maupin | B05B 12/122 239/69 |
| 2017/0107704 | A1 * | 4/2017 | Wang | E03C 1/057 |
| 2017/0296727 | A1 * | 10/2017 | Burbank | A61M 1/165 |
| 2018/0263432 | A1 * | 9/2018 | Yang | A47K 5/1217 |
| 2018/0338649 | A1 * | 11/2018 | Perlas | A47K 5/12 |
| 2020/0320330 | A1 * | 10/2020 | Ophardt | G06V 10/44 |
| 2021/0308290 | A1 * | 10/2021 | Thorne | A61L 2/0088 |
| 2021/0369880 | A1 * | 12/2021 | Newell | A47K 5/12 |
| 2021/0401239 | A1 * | 12/2021 | Buell | G06K 7/10237 |
| 2022/0001046 | A1 * | 1/2022 | Imai | A61L 2/24 |
| 2022/0008592 | A1 * | 1/2022 | Smith | A61L 2/0088 |
| 2022/0008593 | A1 * | 1/2022 | Smith | E03C 1/057 |
| 2022/0015584 | A1 * | 1/2022 | Khan | G06K 7/1413 |
| 2022/0072177 | A1 * | 3/2022 | Depiere | A61L 2/0088 |
| 2022/0106087 | A1 * | 4/2022 | Cousineau | A61L 2/0088 |
| 2022/0288616 | A1 * | 9/2022 | Larry | B05B 11/1073 |
| 2022/0322890 | A1 * | 10/2022 | Bijari | B67D 1/0004 |

FOREIGN PATENT DOCUMENTS

| | | | |
|---|---|---|---|
| WO | WO-2012103284 A1 * | 8/2012 | ............... A61L 2/16 |
| WO | WO-2022046024 A1 * | 3/2022 | |
| WO | WO-2022048725 A1 * | 3/2022 | |

* cited by examiner

RAPID TOUCHLESS AUTOMATIC DISPENSING STATION APPARATUS, SYSTEM, AND METHOD This application claims the benefit of U.S. Provisional Application No. 63/108,708, filed Nov. 2, 2020.

TECHNICAL FIELD

This application relates generally to a dispensing station apparatus, system, and method for liquid personal hygiene product, including, but not limited to, liquid (including gel) soap, sanitizer, disinfectant and/or cleanser, such as for sanitizing, disinfecting or cleaning one's hands, and, more particularly, that is touchlessly automatically operable to dispense a discrete quantity of the liquid personal hygiene product responsive to sensed presence of a person's hand along a predetermined dispensing path, including rapidly in succession responsive to placement of a succession of hands placed in the path. The apparatus can optionally be modular, to enable configuring to include one or more dispensing stations at multiple positions and heights.

BACKGROUND ART

The disclosure of U.S. Provisional Application No. 63/108,708, filed Nov. 2, 2020, is hereby incorporated herein in its entirety by reference.

Currently known dispensing stations for personal hygiene products include those that utilize a reservoir containing a quantity of the product above a piston operated pump operable to dispense discrete quantities of the product onto a person's hands placed in a discharge path of the product below the pump. Advantageously, placing the reservoir and pump above the discharge path of the product enables use of gravity for feeding the product. This also enables placing a lever, handle, or other manual pump actuator beside the discharge path. However, during times of heightened concern for presence of surface borne diseases, such manual pump activators can be a source of infection and are thus disfavored.

Powered, automatically actuated pump driven sanitizer dispensers are widely commercially available. They typically use a sensor to detect presence of a person's hand beside and below a dispensing nozzle. The detection next to the nozzle is necessary, as a reservoir or container of the personal hygiene product and the pump are located above the nozzle, leaving no room for sensor apparatus to sense a hand directly in the dispensing path of the nozzle. The main reason to locate the nozzle under the pump and reservoir is to take advantage of gravity so that the pump uses less power. Also, the pump is a piston type, so as to serve as a closure or valve to prevent leakage of the hygiene product when the dispenser is not in use. Power conservation is desirable as the energy is often provided by a battery or batteries. A disadvantage of using a piston pump is that the reciprocating piston action requires a stroke to draw a discrete quantity of the product into the pump, and a second reverse stroke to discharge the product from the pump. Locating the reservoir above the pump also places practical limitations on the maximum size of the reservoir.

Commercially available sensors commonly used in the known personal hygiene product dispensing stations include light and/or motion detectors, e.g. signal emitting devices with a sensor that detects a reflected portion of the emitted signal, i.e., infrared, passive infrared, ultrasonic, or similar detectors. The sensor is typically set to periodically operate at discrete intervals, for instance ½-1 second, to conserve energy. However, the location of the reservoir, which can be large, e.g., up to 1 liter in capacity, as well as the pump, above the dispensing nozzle, can obscure the nozzle and thus make the location of the dispensing of the hygiene product less apparent, particularly when viewed from above as is common for hand sanitizing and soap dispensing stations. The combination of the delay resulting from the long sensing interval, and the sensing region being beside the dispensing path, can create confusion as to whether the station is operational, and users will often wave or otherwise position their hands to activate the pump then miss the dispensed product with the hand, resulting in wasted product and dissatisfaction. This requires clean up and can be a particularly common occurrence when the users are children.

As an alternative arrangement, other touchless soap dispensers for placing on a counter or attaching to a wall, having a battery powered pump module that mounts directly to a soap bottle or other reservoir (pump directly above, beside, or below the bottle, in a compact package, are also known. These units generally have a dispensing nozzle disposed under a dispensing spout that also holds a sensor for sensing a hand in a wide area below the nozzle and beside the reservoir. The reservoirs are typically of small capacity for personal use, and the large width of the sensing region means that some hands will not receive soap, particularly if only a peripheral portion of the hand is sensed. These dispensers are advertised to dispense soap within a small fraction of a second of sensing a hand, which is relatively easy to achieve given the compact size of the package and resultant short vertical distance that the soap must travel to be dispensed.

As another alternative arrangement, it is also known to use pressurized reservoirs or containers of various products, having a touchless automatic valve mechanism on top. Reference in this regard, Walters et al., U.S. Pat. No. 9,527,656B2 which discloses a touchless dispenser that uses a control circuit board having a sensor arrangement disposed about a product dispensing nozzle. The circuit board and nozzle along with an associated valve and batteries, are carried atop a pressurized product container. The sensor is located closely to the dispensing nozzle to sense presence of a hand proximate to the nozzle. This arrangement is advantageous as the dispensing nozzle and sensor are co-located to better detect a person's hand when positioned proximate to the dispensing nozzle. This dispenser, as the container is pressurized, does not require or utilize a pump. Only one dispenser per product container is disclosed. This dispenser is disadvantageous as pressurized containers are typically more costly, less environmentally friendly, and have a relatively low product holding capacity. Also, when the users are mostly children, and it is desired to keep the dispensing apparatus from being contaminated by contact with user's dirty hands, requiring close proximity to the dispensing nozzle to trigger the dispensing of the product may not be ideal.

With the advent of widespread communicable diseases, touchless sanitizing/disinfecting/cleaning stations are seeing increased demand. It is desirable for the stations to overcome one or more of the limitations set forth above, function intuitively, and be adaptable for a range of applications, including, but not limited to, for use by users of various heights, and by queues of users in rapid succession, such as school children, shoppers, office and plant workers, concert goers, restaurant patrons, and the like.

What is sought is a touchless automatic personal hygiene product dispensing station apparatus, system, and method, that overcomes one or more of the limitations and disadvantages set forth above.

SUMMARY OF THE INVENTION

What is disclosed is a touchless automatic personal hygiene product dispensing station apparatus, system, and method that overcomes one or more of the limitations and disadvantages set forth above.

Preferred aspects of the invention comprise a structure carrying a reservoir of a personal hygiene product located below, and in fluid communication with, one or more dispensing stations, and a sensing/dispensing system proximal the respective dispensing stations, operable automatically in conjunction therewith, and referred to herein sometimes as a sensing/dispensing station, to dispense predetermined small quantities of the product along associated dispensing paths, virtually immediately responsive to detection of presence of a person's hand in the dispensing path or paths, including simultaneously, and in rapid succession for each sensing/dispensing station. The sensing time and dispensing speed achieved with the invention combine to allow dispensing the product to a continuous succession of hands to avoid dispensing delays, e.g., due to pump cycle times, reduced pressurization resulting from inactivity or high volume use, poor/inaccurate hand sensing, and the like, that can result in decreased efficiency, delays that have been observed to create confusion and/or doubt in users' minds as to whether the station is operational, so that persons such as school children, shoppers, office and plant workers, concert goers, restaurant patrons, and the like, are less likely to be dissuaded or discouraged from using the station and less product will be wasted from missing the users' hands, particularly if they have the habit of waving their hands to activate dispensing as a result of unsatisfactory or poor experiences with other dispensers.

As another aspect of the invention, the personal hygiene product dispensing station apparatus can be modular in multiple respects, to enable configuring to include one or more sensing/dispensing stations at different multiple positions, for instance, on opposite sides of the structure of the apparatus, e.g., on three or four sides, and/or at different heights, for instance, one or more stations at one height for younger elementary school age students, and one or more at another height or heights for older students and/or adults. In this latter regard, all or a portion of the structure can be height adjustable, for instance, telescoping, for accommodating different hand heights, at different times. As a non-limiting example, the apparatus can have one or more sensing/dispensing stations at one height on a first or lower section of the structure, and one or more on an upper section that is telescoping in relation to the first section. As another modularity option, the sensing/dispensing stations can be selectably attached to different locations on the structure, to configure for different/changing applications, as explained below. As another optional aspect, the housing can be mobile, e.g., on wheels, skids, etc.

As another aspect, one or more upstanding germ shields or barriers can be removably or permanently installed on the structure between the sensing/dispensing stations. As still additional aspects, the structure can contain a trash receptacle, and one or more accessory dispensers, such as a glove and/or mask dispenser, or a digital device such as a tablet or graphical user interface (see FIG. 12), can be attached to the exterior, and provide an interface, such as a user login or visual image record, facial recognition, card reader, or the like, for a variety of purposes such as monitoring, contact tracing or the like.

As to operational aspects, the touchless automatic personal hygiene product dispensing station apparatus is touchlessly automatically operable upon sensing presence of all or a portion of a person's hand along a predetermined elongate product dispensing path, to immediately and rapidly dispense a small, discrete quantity of the liquid personal hygiene product, e.g., a fraction of one ounce, or a gel or foam, along the path and onto the hand for use by the person to sanitize his or her hands or perform some other personal hygiene function. The hand sensing activates the dispensing of the product within a fraction of a second to facilitate rapid repeated or successive sensing and dispensing, for high volume applications, e.g., to a succession of people, such as a line of school children, shoppers, concert goers, movie goers, sporting event ticket holders or players, airline, train, ferry or boat passengers, and the like, so that their movements are not significantly delayed by the sanitizing step and the persons are not inconvenienced.

According to a first preferred embodiment of the invention, the touchless automatic personal hygiene product dispensing station apparatus comprises a housing carrying a reservoir for receiving and holding a first quantity of a liquid personal hygiene product. An enclosed liquid path extends from the reservoir to a pump or pumps of one or more sensing dispensing stations disposed above the reservoir, each pump being controllably operable in a prolonged priming mode to create a partial vacuum condition within the enclosed fluid path to that pump to draw the liquid personal hygiene product from the reservoir up through the enclosed liquid path into the pump. Each pump has an inactive standby mode to pinch closed the enclosed liquid path sufficient to hold the liquid personal hygiene product therein. The pump is further controllably operable from the standby mode in a momentary dispensing mode multiple times shorter than the prolonged priming mode to dispense a discrete quantity of the liquid personal hygiene product while creating a partial vacuum condition in the enclosed liquid path sufficient to draw more of the liquid personal hygiene product from the reservoir into the associated enclosed liquid path to replace the dispensed liquid personal hygiene product. An enclosed dispensing conduit extends from the pump through a dispensing spout attached to the housing, to a dispensing outlet located external to the housing from which the discrete quantity of the liquid personal hygiene product is dispensed to flow down along a predetermined elongate open dispensing path externally of the dispensing conduit and the dispensing spout, for dispensing onto a person's hand or other receiver.

To facilitate immediate and rapid dispensing (in succession if necessary), the enclosed dispensing conduit will preferably have a volume or capacity sufficient to hold one or more multiples of the discrete quantity of the product desired to be dispensed onto each hand, e.g., typically a fraction of an ounce (if the product is foamed so as to expand when dispensed to atmosphere, the quantity in the liquid state will be smaller and the foamed quantity greater), and the pump will be configured to operate in the momentary dispensing mode to discharge just one smaller discrete quantity of the product when activated. The overall enclosed liquid path preferably has an internal volume equal to several multiples of the desired discrete quantity of the product, to be able to dispense a large number of discrete quantities of the product in rapid succession.

According to another preferred aspect, an electrically powered control device is connected in operative control of the pump and comprises an input operable activate the pump to operate in the prolonged priming mode to fill the enclosed liquid path and optionally all or part of the enclosed dispensing conduit with the liquid personal hygiene product, and thereafter deactivate the pump to the standby mode. A touchless input device includes a circuit board, a sensor having an on state to sense presence of a person's hand along a predetermined elongate sensing region external to the sensor when the pump is in the standby mode. Circuitry on the circuit board is automatically operable to immediately initiate operation of the pump from the standby mode in the momentary dispensing mode responsive to the sensed presence of a hand in the elongate sensing region, then to automatically return the pump to the standby mode, or again initiate operation of the pump in the momentary dispensing mode responsive to the sensed presence of another hand in the sensing region. The circuit board is preferably located in or on the dispensing spout to position the sensor in predetermined relation to the dispensing conduit such that the sensor faces down to position and orient the elongate sensing region coincident with the dispensing path such that the sensor will sense the presence of a hand when in the dispensing path, including when spaced a hand span or more below the dispensing outlet within the sensing region.

As a preferred aspect, a peristaltic pump having a self-priming capacity allows the reservoir to be located well below the pump, which provides the additional advantage of a relatively long enclosed liquid path to connect the two to hold a significant quantity of product awaiting dispensing and also facilitate modularity. The holding capacity is in part achieved by pinching closed the portion of the enclosed path, e.g., rubber or plastic tube, by one or more lobes, rollers, or vanes of the peristaltic pump when the pump is not operating. The preferred peristaltic pump thus acts as a mechanical check valve to prevent back flow of the liquid product when the pump is not actively pumping. The pinched closed condition also prevents back flow of vapor or gas through the pump, which back flow would be required to replace the liquid product in the upper region of the enclosed path on the upstream or supply side of the peristaltic pump were the liquid product have a tendency to begin to drain back toward the reservoir when the pump is not operating. Contributing to the maintaining of the liquid product in the enclosed liquid path between the reservoir and pump, will be residual partial vacuum within the path, which will be trapped by the pinched state of the tube within the pump when not operating, e.g., in the standby state or between dispensing individual quantities of the product, and possibly viscous friction between the liquid product and the walls of the tubing of the enclosed path, and capillarity. The pinched state of the enclosed path and other conditions holding the liquid stationary will have the same effect on the liquid in the enclosed liquid path between the pump and the dispensing outlet, and as an additional feature a P-type trap can be employed in that portion of the path. As an additional advantage, as a result, a relatively low power pump can be used and will dispense product virtually upon activation. As a preferred peristaltic pump, one having about a 1-2 inch diameter 3 lobe or roller impeller has been found to dispense a suitable discrete quantity of liquid product for hand sanitizing with a single revolution or less of pump operation.

As another aspect, a suitable sensor for each sensing/dispensing station can comprise a laser, infrared, radio, or ultrasonic signal emitter/receiver capable to sense a hand or hands within a sensing region of several inches in length but having a relatively narrow width similar in width to or just smaller than, a representative hand span. The sensor is preferably mounted so that the elongate sensing region is coincident with or contains the associated dispensing path for the product, so that a hand when sensed will be in the dispensing path. To accomplish this, the sensor is preferably mounted on or in the dispensing spout closely aligned with the dispensing path. The dispensing outlet can be retained on or jointly with, the circuit to achieve desired coincidence of the dispensing path and the sensing region.

A preferred sensor is a laser sensor having an emitter that emits a downward laser signal along a sensing region closely parallel to or coincident with the dispensing path, such that a hand that enters the dispensing path anywhere along the length thereof, including a hand span or more below the dispensing outlet, will be sensed to initiate dispensing of the personal hygiene product along the dispensing path with a high likelihood of landing on the hand. An advantage of a laser signal is that it can have a focused beam similar in sectional extent to the dispensing path so as to be essentially coincident or closely beside the dispensing path, such that a hand must be correspondingly close or within the dispensing path to be sensed. Another advantage is that the laser sensor can have a tuned frequency range that allows the sensor to discriminate the reflected laser light from ambient light, e.g, indoor lighting and natural lighting including bright sunlight, as well as other directed lights, e.g., LED emitted light, that may be present. Another advantage is that the signal can be narrowly focused and thus not dispersed so that a hand will necessarily have to be very close to the dispensing path to be sensed. Further in this regard, it is contemplated that a sensor employed can have 2 or more laser sensing elements or tubes that allow sensing direction of hand motion and the sensor circuitry would be operable to determine whether a hand is moving into the dispensing path or out of it, or both, in a back and forth or waving action, and thusly determine whether to dispense or not

DETAILED DESCRIPTION OF EMBODIMENTS OF THE INVENTION

Figure 1:
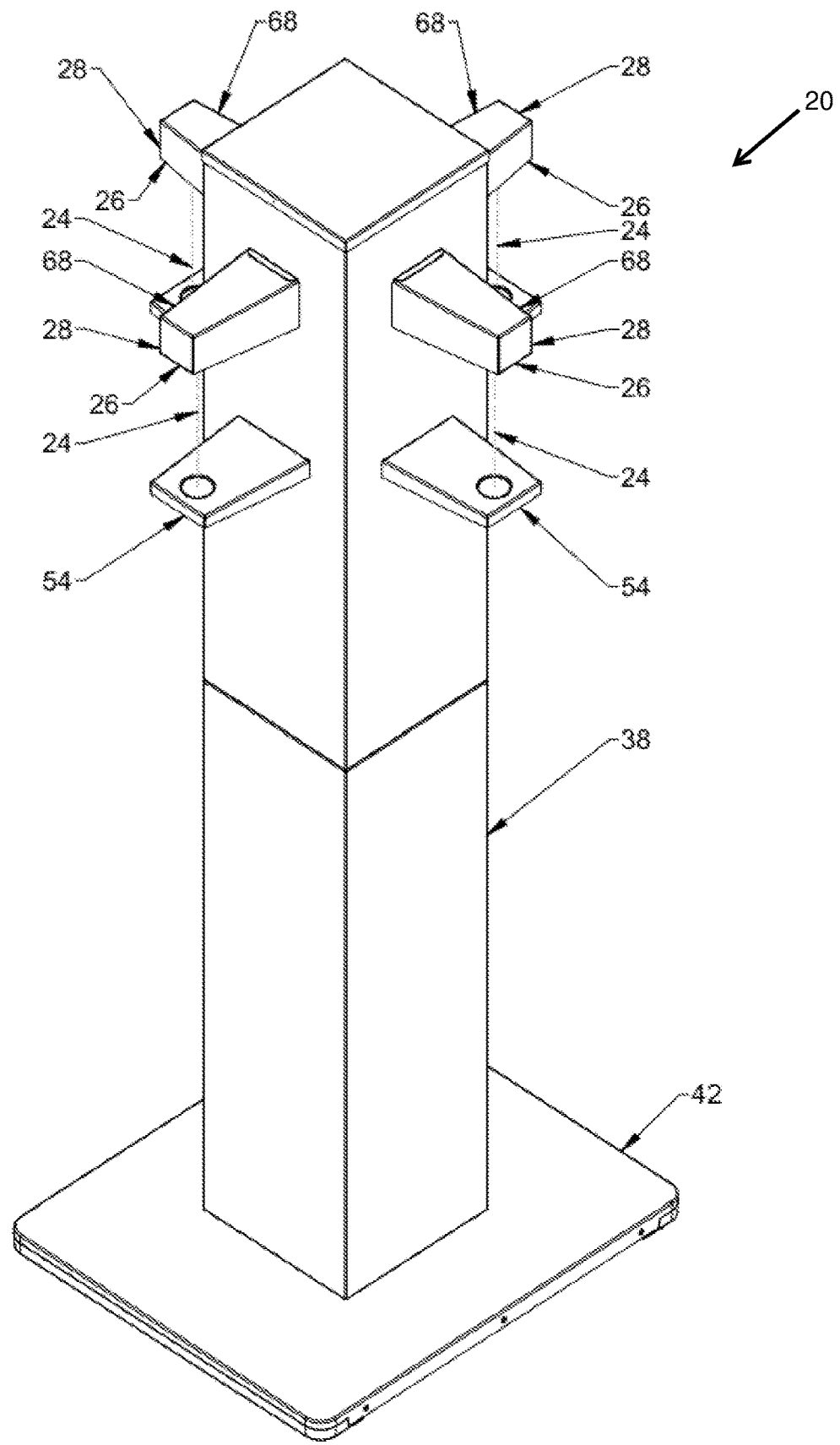
FIG. 1 is a enlarged perspective view of a touchless automatic personal hygiene product dispensing station apparatus constructed and operable according to the teachings of the invention.
Figure 2:
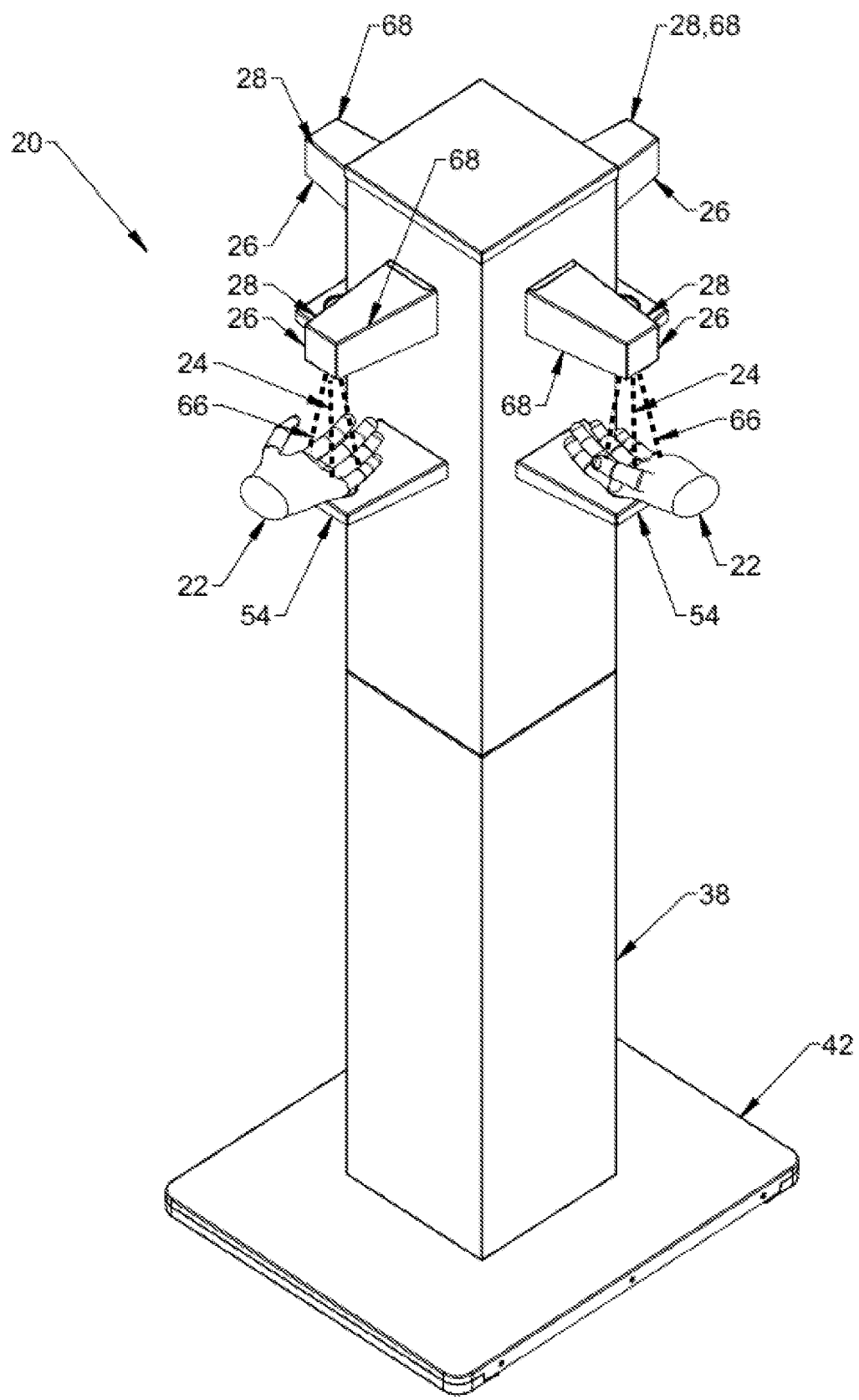
FIG. 2 is another perspective view of the touchless automatic personal hygiene product dispensing station apparatus, illustrating hands within dispensing paths and sensing regions of individual dispensing stations of the apparatus.
Figure 3:
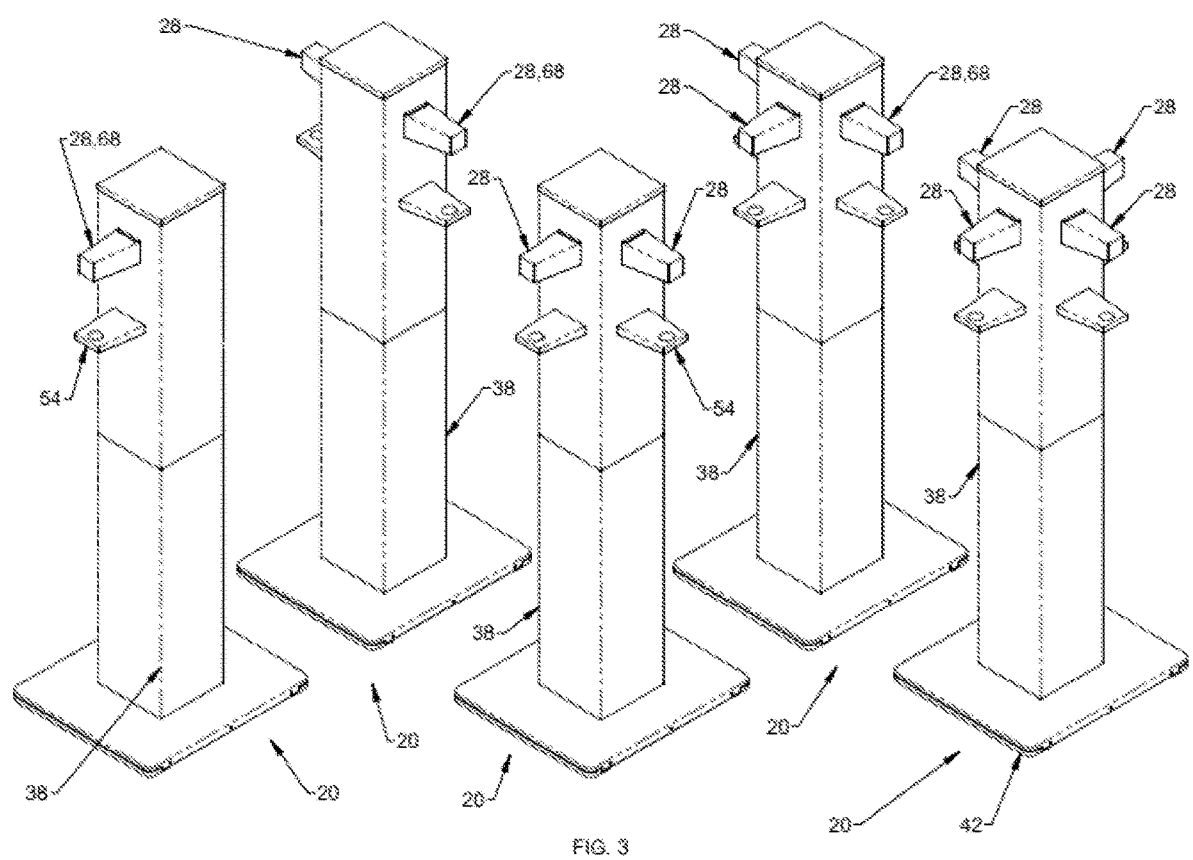
FIG. 3 shows several alternative embodiments of the apparatus of the invention, including 1, 2, 3, and 4 dispensing stations.
Figure 4:
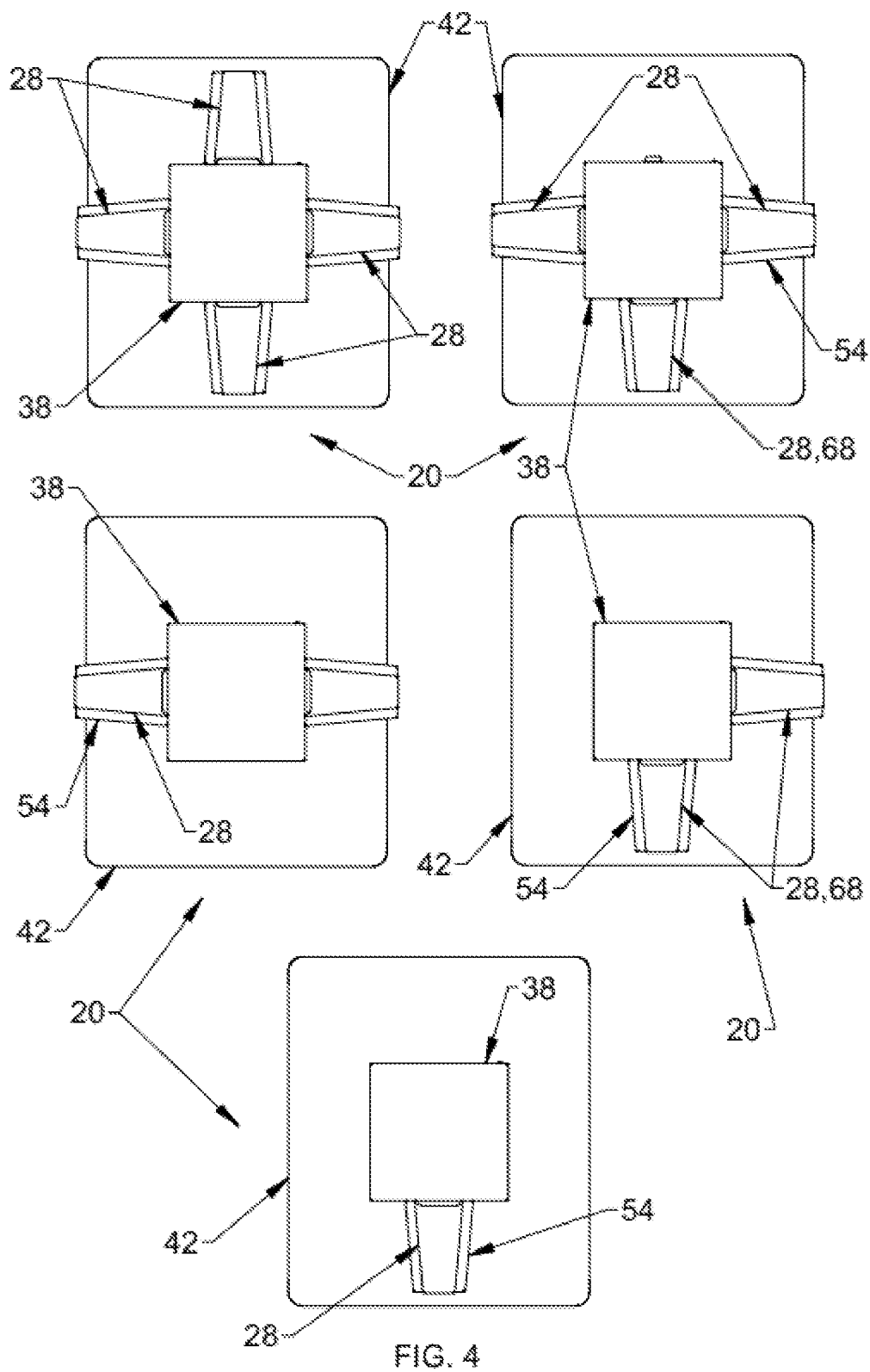
FIG. 4 is a top view of the alternative apparatus of FIG. 3.
Figure 5:
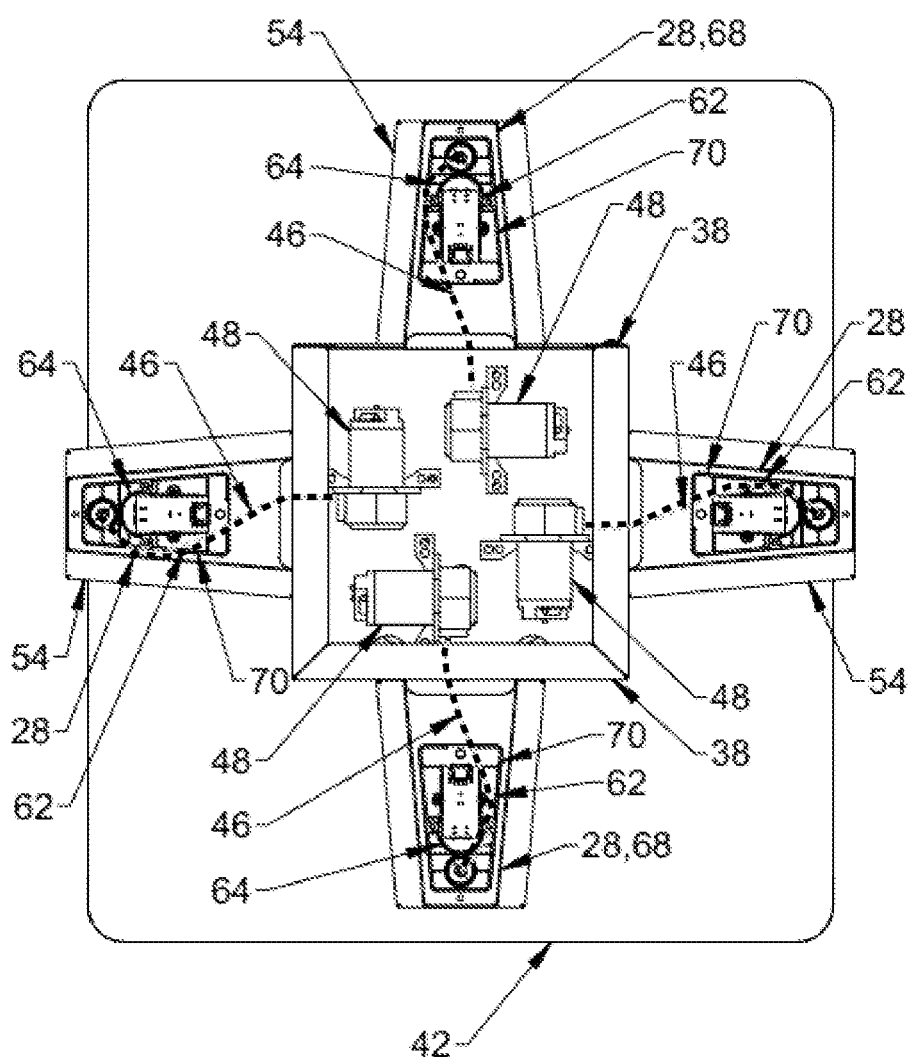
FIG. 5 is a top view of the apparatus of the invention, including 4 of the dispensing stations, with top panels removed to expose internal aspects thereof, including pumps circuit boards of touchless sensor circuits, and showing routing of enclosed liquid paths.
Figure 6:
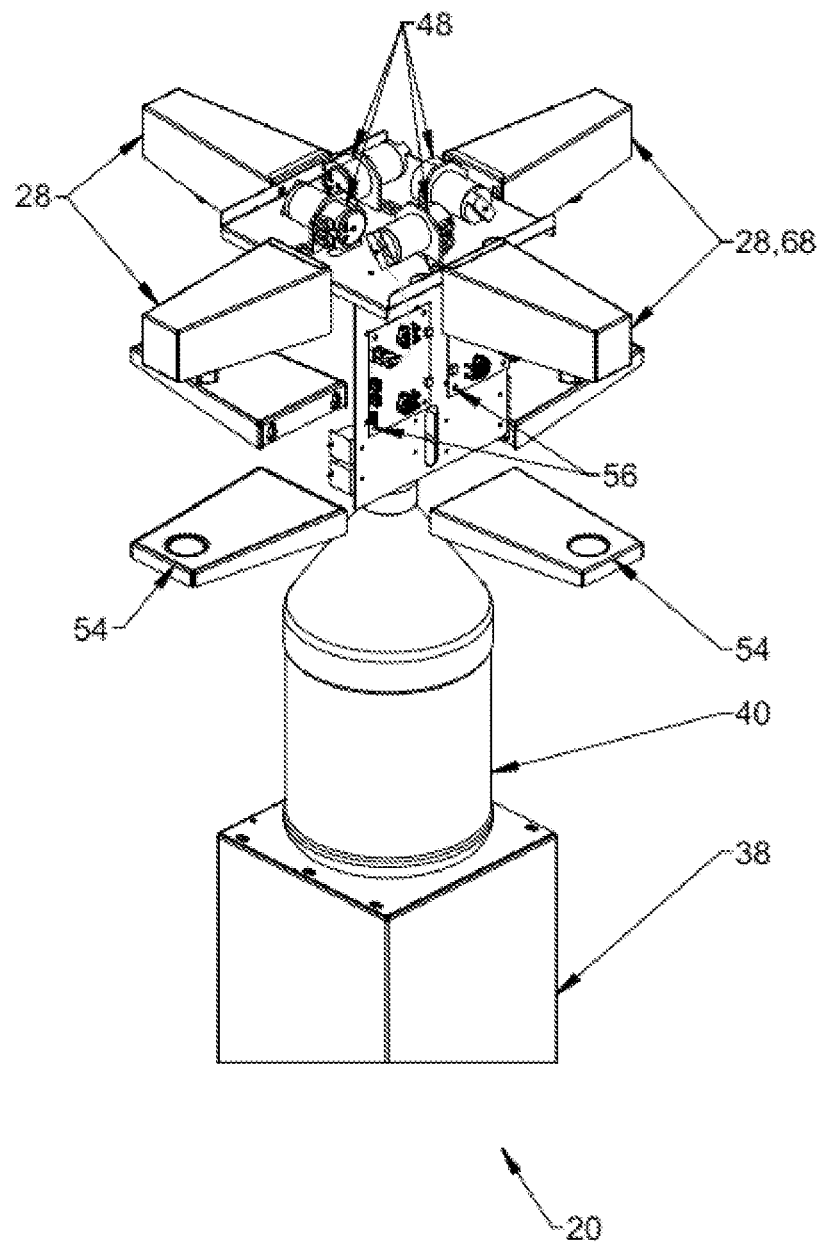
FIG. 6 is a perspective view of the apparatus of the invention, including 4 of the dispensing stations, with upper panels of a housing removed to expose a reservoir, an internal vertical panel carrying control devices, an internal horizontal panel carrying pumps, and dispensing station apparatus, including dispensing spouts, and catch basins.

Referring to FIGS. 1-17, a touchless automatic personal hygiene product dispensing station apparatus 20 of a system and method of the invention is touchlessly automatically operable upon sensing presence of all or a portion of a person's hand 22 (FIG. 2) along a predetermined elongate product dispensing path 24 (FIGS. 1, 2, 8, and 13), to immediately and rapidly dispense a small, discrete quantity of the liquid personal hygiene product, e.g., a typical quantity required to effectively sanitize or disinfect a person's hand, which may be as a non-limiting example, a fraction of one ounce of liquid, or a gel or foam, along the path 24 and onto the hand 22 for use by the person to sanitize his or her hands or perform some other personal hygiene function. By configuring the apparatus 20 of the invention to locate the hand sensing along the dispensing path 24, including spaced substantially, e.g., a hand span or more from the dispensing outlet 26, and then immediate activate dispensing the product, that is, within a fraction of a second of the hand 22 being sensed, there is increased likelihood that that the dispensed product will be at least largely dispensed onto the hand 22 before the hand is moved or removed. This combination of sensing along the elongate dispensing path 24 and immediately responsively dispensing, facilitates rapid repeated or successive sensing and dispensing, for instance for dispensing hand sanitizer or disinfectant to a succession of people, such as a line of school children, shoppers, concert goers, movie goers, sporting event ticket holders or players, airline, train, ferry or boat passengers, and the like, so that their movements are not significantly delayed by the sanitizing step and the persons are not inconvenienced. The greater likelihood of the sanitizer or other product reaching a user's hand, can be particularly important for children and other persons who may be fidgety, inattentive, or in a hurry, as well as persons not familiar with the dispenser who may have a tendency to waive their hand about under what appears to the be dispensing outlet, which often results in the dispensed product missing the hand.

Figure 17:
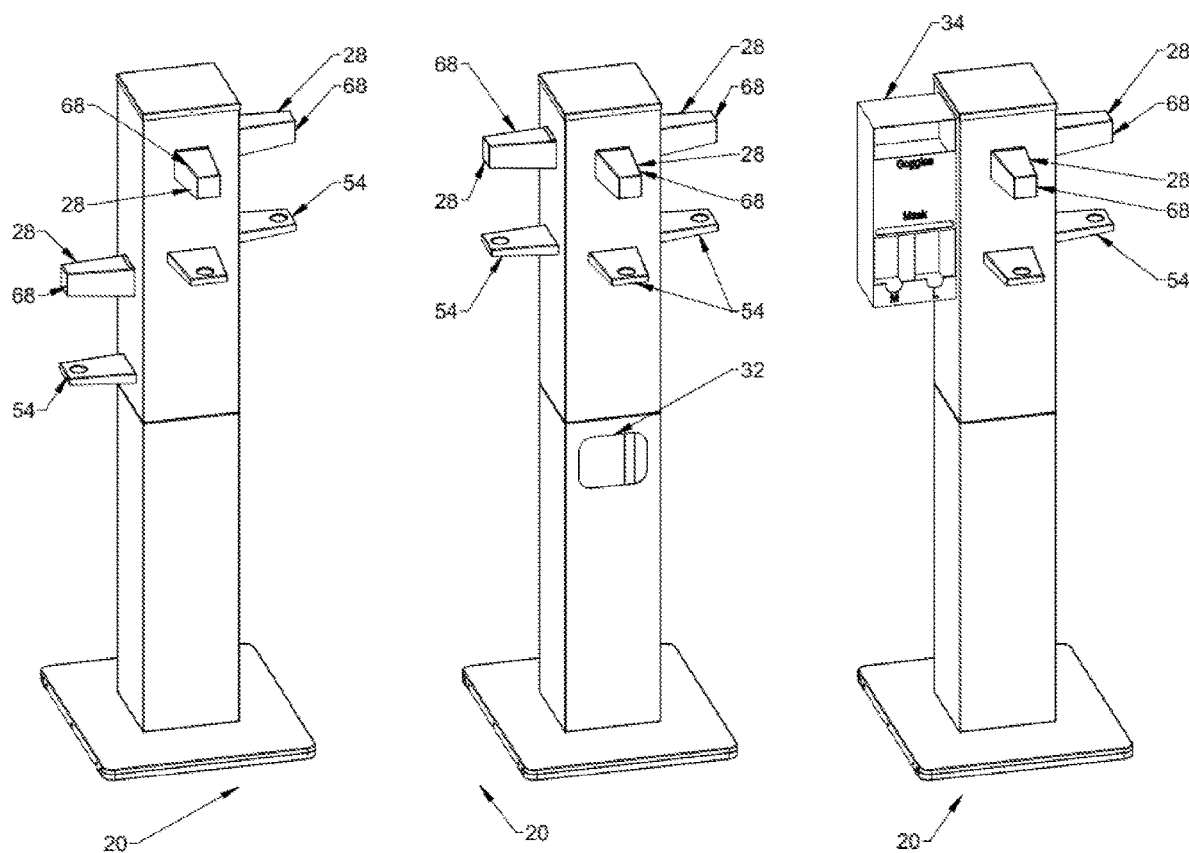
FIG. 17 are perspective views showing alternative apparatus of the invention having dispensing stations at different heights, a trash receptacle in a lower region, and an attached accessory which is a dispenser for goggles and masks.

As an optional aspect of the invention, the apparatus 20 can be modular, to enable configuring to include one or more sensing/dispensing stations 28 at multiple positions, for instance, on opposite sides of the structure of the apparatus 20 or on four sides, and/or at different heights, for instance, one or more stations 28 at one height for younger elementary school age students, e.g., 30-32 inches or so, and one or more at another height or heights for older students and/or adults, e.g., 42-48 inches or so. In this latter regard, all or a portion of the apparatus 20 can be height adjustable, for instance, telescoping, for accommodating groups of people of different heights, at different times, see FIG. 17. As a non-limiting example, the apparatus 20 can have one or more sensing/dispensing stations at one height on a first or lower section of the structure, and one or more on an upper section that is telescoping in relation to the first section. As another modularity option, the sensing/dispensing stations 28 can be selectably attached to different locations on the structure, to accommodate different/changing applications, as explained below. As another optional aspect, one or more upstanding germ shields 30 or barriers can be removably or permanently installed on the structure between sensing/dispensing stations 28, as shown in FIGS. 13-16. As shown in FIG. 17, as still another option, the structure of apparatus 20 can contain a trash receptacle 30, and one or more accessory dispensers 34, such as a glove dispenser, or a digital device 36 such as a tablet or graphical user interface (see FIG. 12), can be attached to the exterior, and provide an interface, such as a user login or visual image record, facial recognition, card reader, or the like, for a variety of purposes such as monitoring, contact tracing or the like.

According to another aspect of the invention, the structure of the apparatus comprises a housing 38 that carries a reservoir 40 containing a first quantity of the liquid personal hygiene product, which will equate to a large number of quantities of the product to be individually dispensed onto user's hands. As non-limiting examples, the housing 38 can be of bent and/or stamped sheet metal, molded plastics, or wood, or other common building material, and can be constructed as an upstanding column, cylinder, panel, or box, having a height sufficient for locating one or more sensing/dispensing stations 28 at about the height of expected users' hands with the arm relaxed and palm facing up or down, or which can be easily reached by extending the arm, e.g., just lower than shoulder height. It is generally desired to have the reservoir 40 lower as opposed to above the dispensing outlet 28, as it is contemplated that when full it will contain a gallon or more of the liquid hygiene product, which can weigh 8 pounds or more, and so, less lifting will be required, and the center of gravity of the structure will be an adequate distance lower than the sensing/dispensing station(s) 28 to reduce possibility of tipping of the structure. This larger quantity is contemplated to be advantageous as it will require less often refilling or replacement of the liquid personal hygiene product, particularly for large volume applications, e.g., schools, stores, airports, train stations, cruise ships, theaters, sports locations, and the like. The lower location also facilitates easier viewing of the dispensing outlet 26. As non-limiting examples, the reservoir 40 can be a refillable cavity, or a removable tank, jug, bottle, or the like, supported on or in the lower region of the housing 38.

Figure 11:
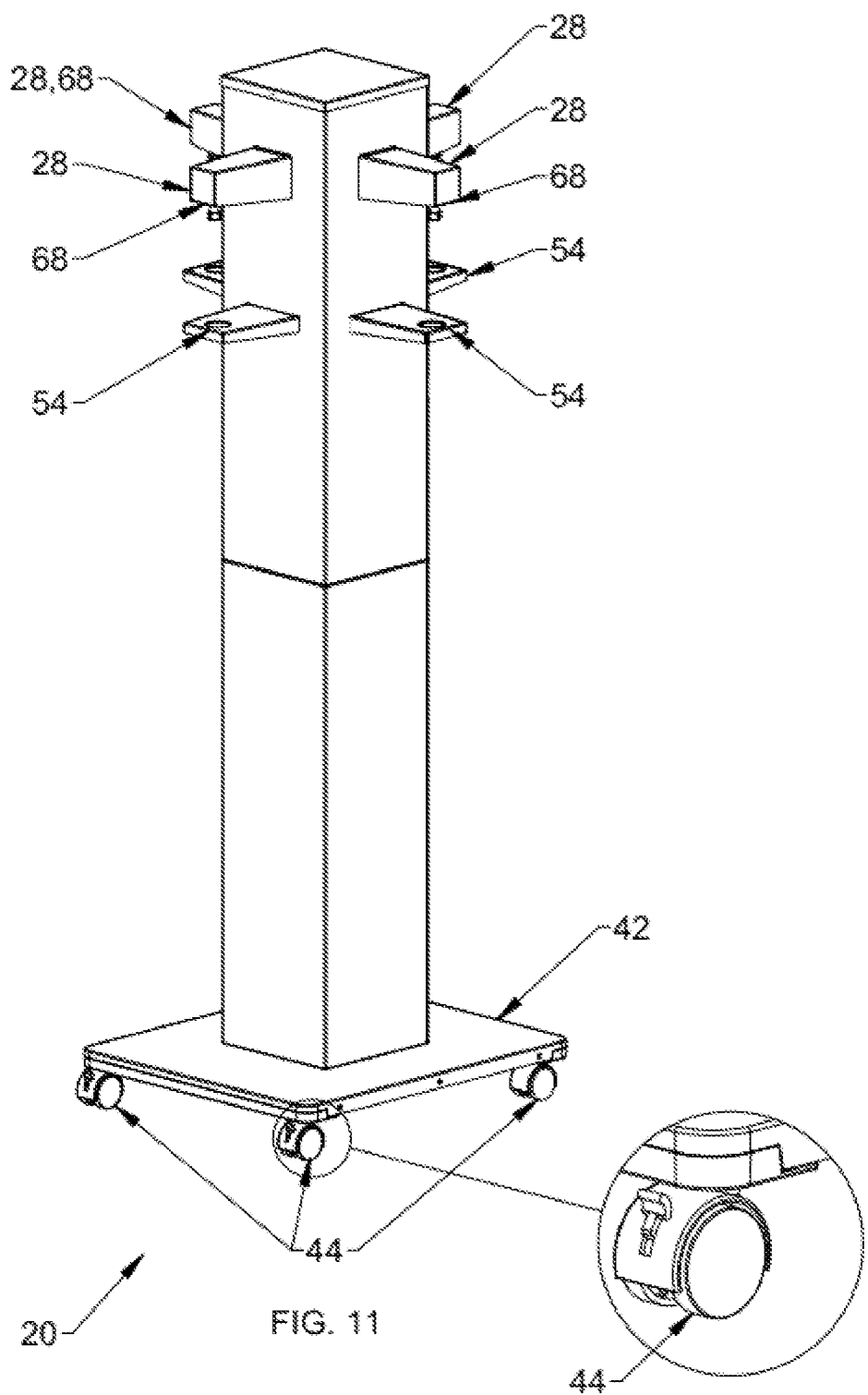
FIG. 11 is a perspective view of an apparatus of the invention, supported on caster wheels.
Figure 12:
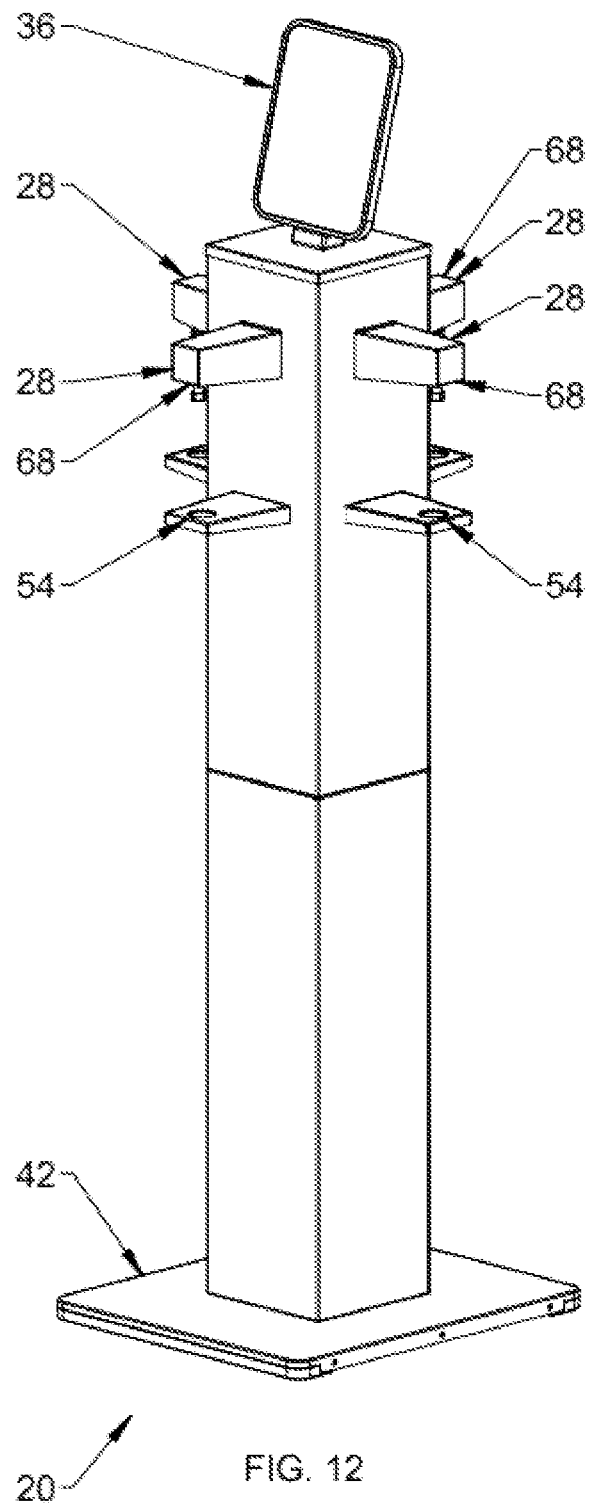
FIG. 12 is a perspective view of an apparatus of the invention, including an accessory which is a digital tablet.
Figure 13:
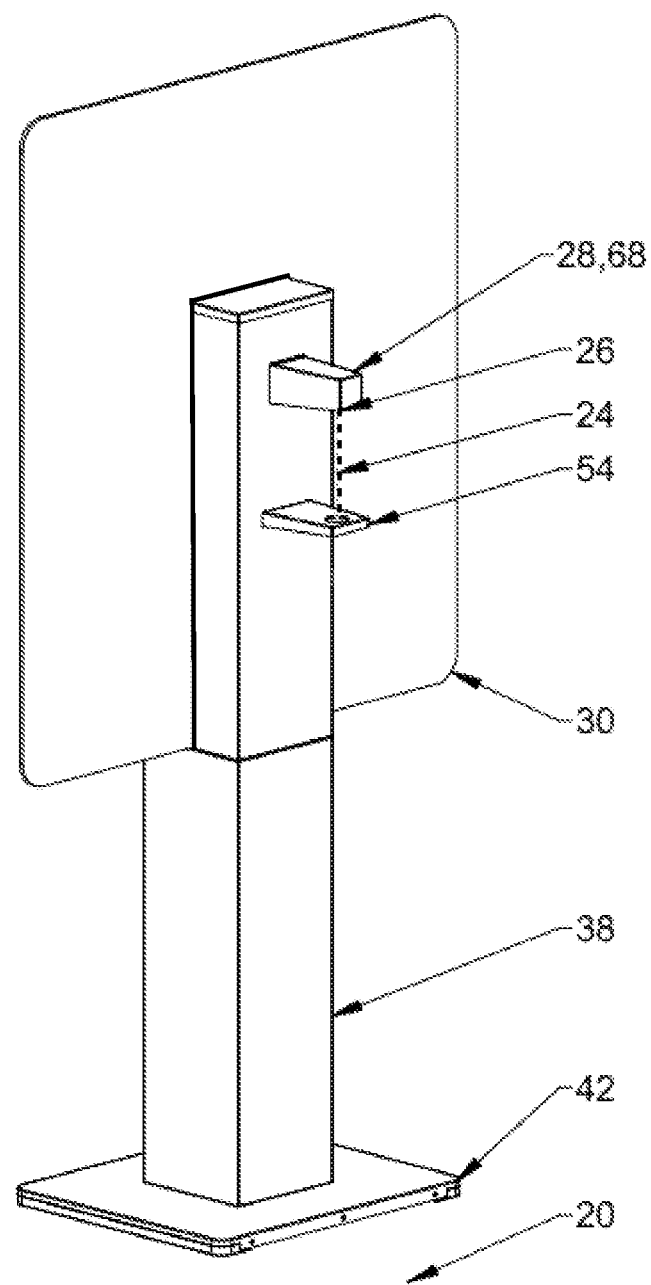
FIG. 13 is a perspective view of an apparatus of the invention, having an upstanding germ shield installed between dispensing stations thereof.
Figure 14:
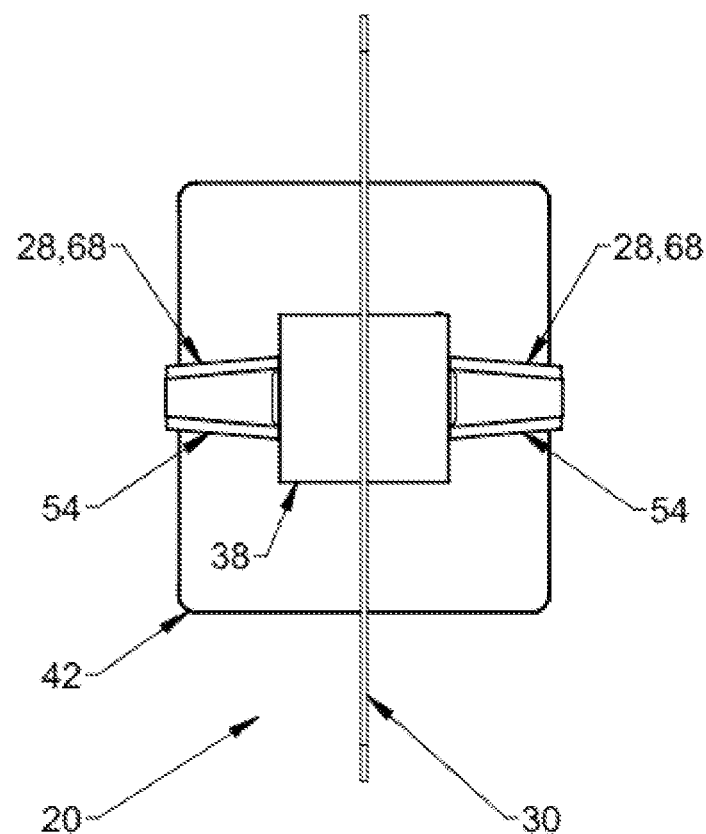
FIG. 14 is a top view of the apparatus of FIG. 13.
Figure 15:
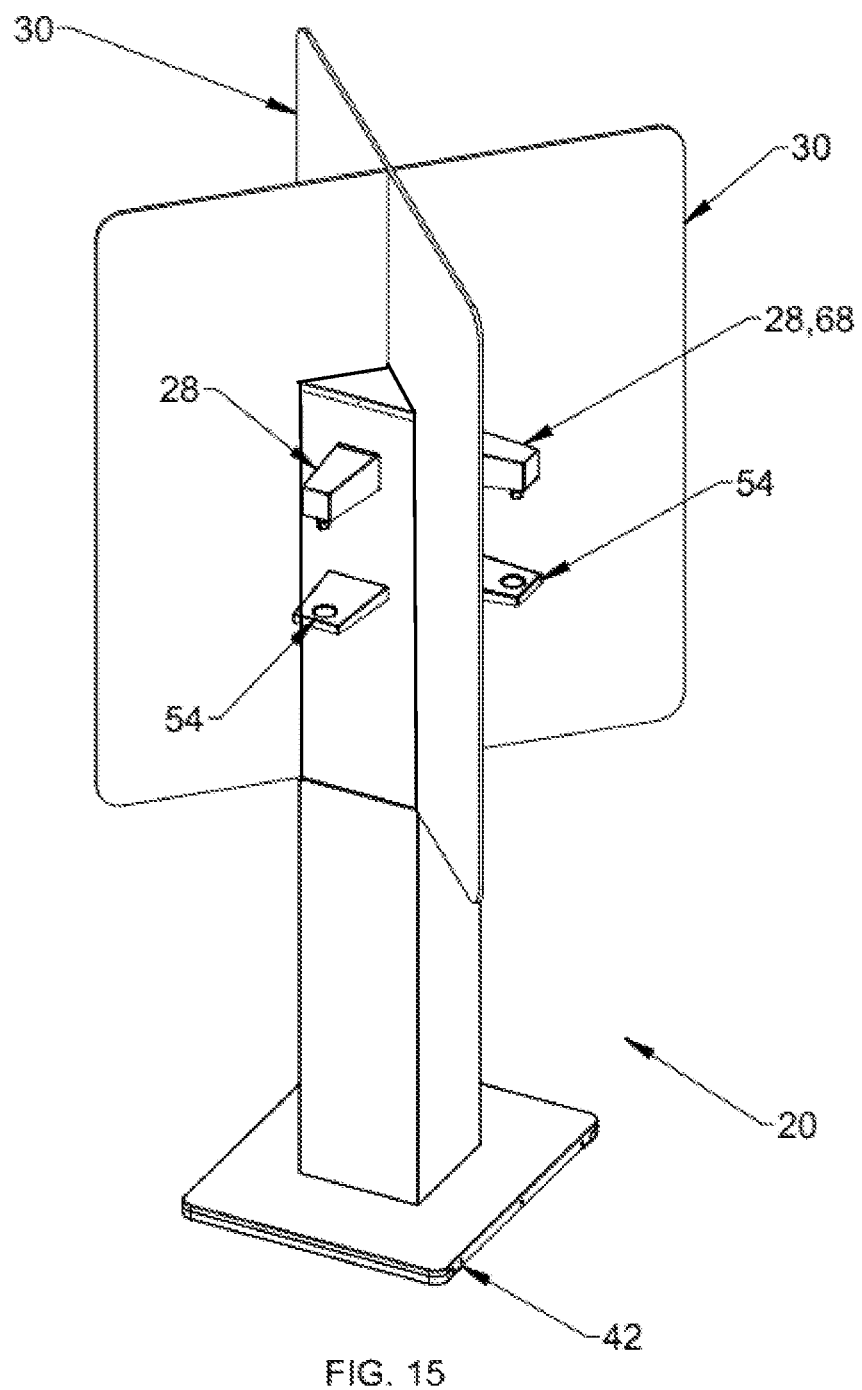
FIG. 15 is a perspective view of another apparatus of the invention, having 4 dispensing stations, and upstanding germ shields therebetween.
Figure 16:
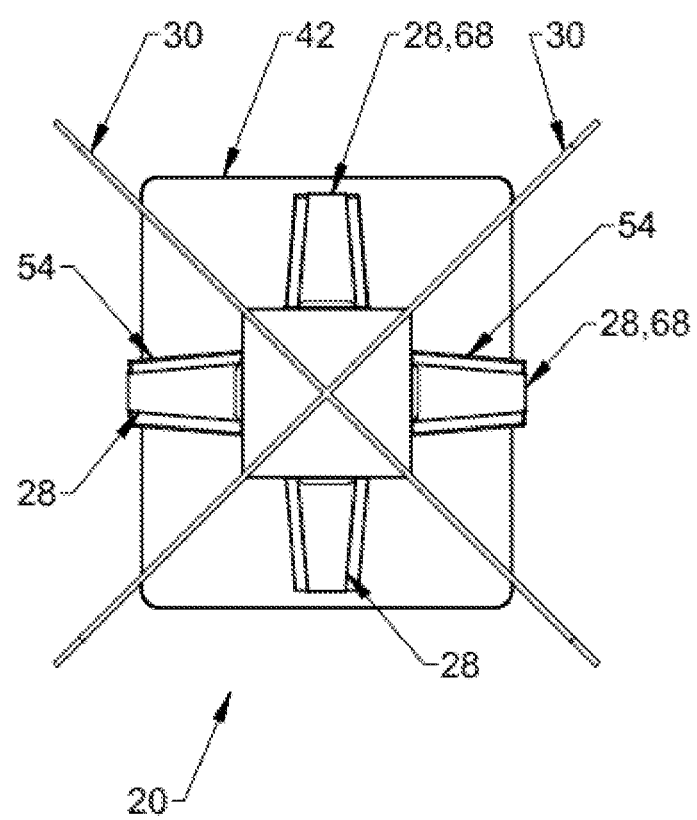
FIG. 16 is a top view of the apparatus of FIG. 15.

As another optional aspect, the housing 38 can be constructed to be stationary, e.g., attached or fixed to a wall, floor, or other structure, e.g., base or pedestal 42; or it can be mobile, e.g., on wheels 44, skids, etc, see FIG. 11.

As another aspect, the apparatus 20 comprises at least one enclosed liquid path 46 (FIGS. 5, 7, 9, 10) extending upward from the interior cavity of the reservoir 40 to a pump 48 (FIGS. 5, 6, 7, 9) supported on the housing above the reservoir 40. This liquid path 46 can be constructed of a material suitable for carrying the liquid personal hygiene product such as, but not limited to, tubing, such as metal or flexible plastics tubing, piping, or the like, capable of operation under partial vacuum. The liquid path 46 can comprise a single tube or pipe, that extends through the pump 48 in the instance of some peristaltic pumps having impeller lobes or rollers that compress flexible tubing while the impeller 50 (FIG. 9) rotates, or it can connect to a suitable fitting on another style pump, such as a barbed, threaded, or quick connect fitting, to an inlet port in connection with an internal passage of the pump. The latter style of pump can accordingly have a discharge port with a suitable standard fitting for connection to a dispensing portion 52 or section of the liquid path 46 or conduit.

Figure 7:
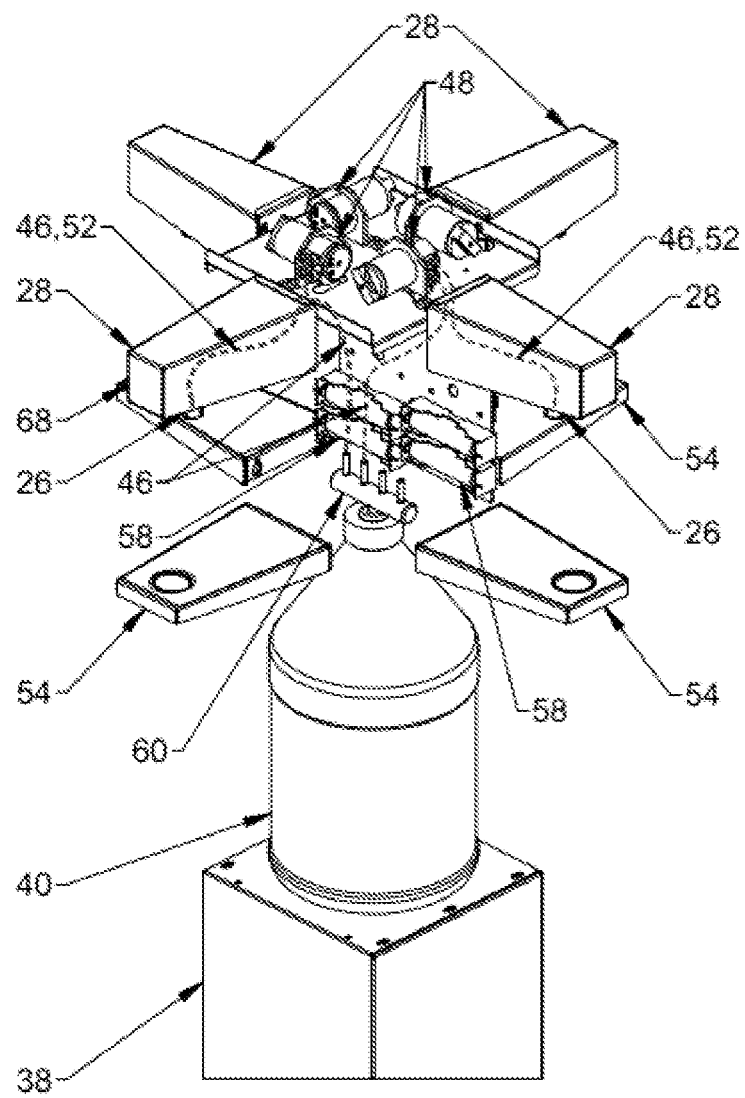
FIG. 7 is another perspective view of the apparatus of FIG. 6 with the panels of the housing removed, exposing the reservoir, a manifold, the vertical panel carrying battery holders, the pumps, dispensing spouts, and catch basins.
Figure 8:
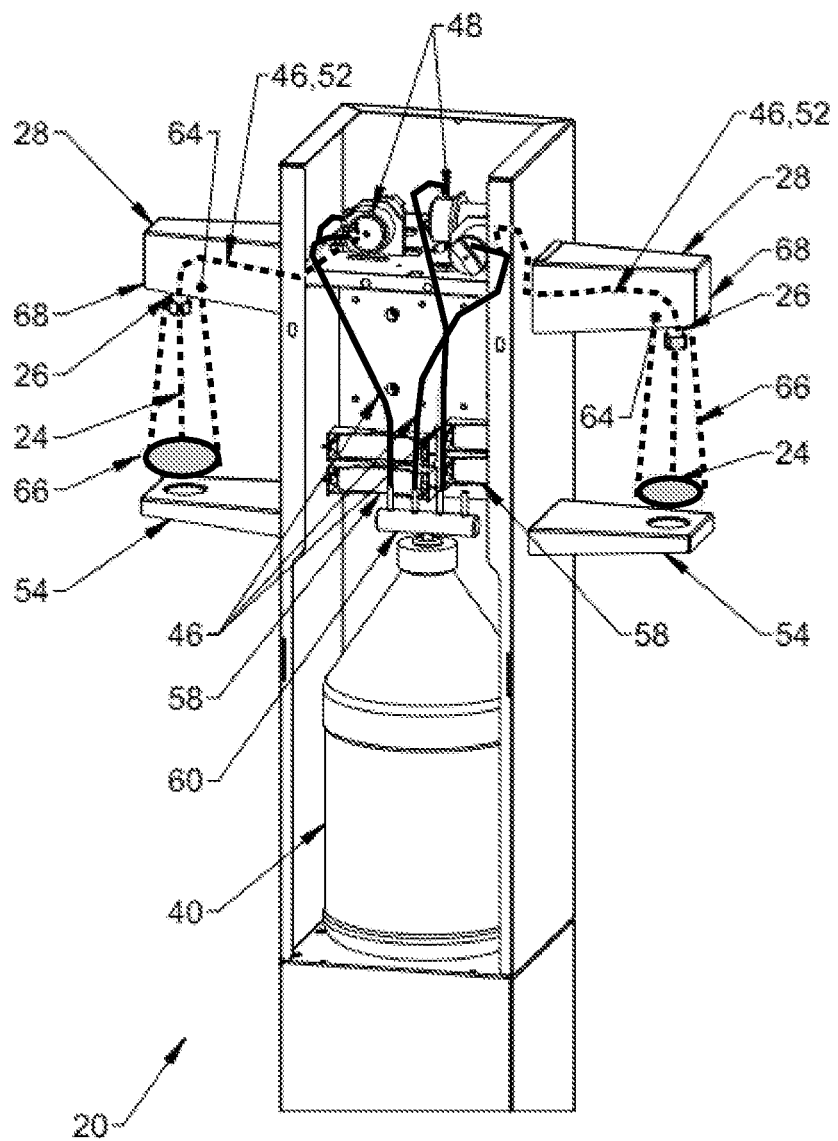
FIG. 8 is an enlarged perspective view of a variant of the apparatus having 2 of the dispensing stations on opposite sides of the housing, showing an upper panel of the housing removed to reveal the reservoir, battery holders, pumps, and internal enclosed liquid paths, as well as illustrating the relationship between product dispensing paths of the stations and hand sensing regions.

As shown in FIGS. 7 and 8, the dispensing portion 52 or section of the liquid path 46 leads to a dispensing outlet 26 from which the liquid personal hygiene product will be discharged or dispensed along a predetermined product dispensing path 24 at a selected location external to the housing 38. Further in this regard, it is preferred that the dispensing outlet 26 will be configured such that the product dispensing path 24, in addition to being elongate, will be relatively narrow in section, most preferably a thin stream, so as to reasonably be expected to land on a person's hand located anywhere within or along the dispensing path 24, and not be wasted. A catch basin 54 for the dispensed product that fails to land on a hand can be located an appropriate distance below the dispensing outlet 26, as shown, and comprises part of the dispensing station 28. The basin can connect to a waste receptacle in the lower region of apparatus 20, if desired.

Further in the above regard, it is expected that for some applications where a high volume of users are expected during a very short interval of time, particularly, when hurried in school settings such as when entering the school or changing classes or at lunchtime or restroom breaks, transportation settings such as when embarking or disembarking aircraft or trains, at concerts and movies and sporting events, users, and particularly children, may not be attentive to the personal hygiene task. This has been observed to make it critical that hand sensing and liquid product dispensing occur reliably quickly, both for users individually, and successive users. In regard to the former, it has been found advantageous for the sensing to occur quickly and virtually immediately followed by dispensing. Regarding the latter, after dispensing to the hand of one user, the sensing device should be able to quickly distinguish the interval between normal movement and removal of a person's hand onto which product has been dispensed, and a successive user's hand entering the dispensing path. In this regard, it has been observed that users are often dissatisfied and dispensing quality reduced by known dispensing apparatus that take "too long", e.g., a second or more, to sense presence of a hand, particularly another person's hand that enters the sensing region after the station has just dispensed product onto a predecessor's hand, and then actuate a pump, such as a piston pump, to cycle so as to draw a quantity of the hygiene product into the pump, then discharge it, which has been observed to take an additional second or more.

To avoid dissatisfaction and meet the critical necessities for accurately sensing hands and rapidly dispensing the hygiene product to successive users, it has been found that an advantageous approach is to have a capacity to dispense a relatively large number of relatively small quantities of personal hygiene product in rapid succession, and to closely combine the sensing with the dispensing, that is, to perform the functions within essentially the same location, defined as anywhere along the length of the dispensing path 24 of the product within convenient reach by a user.

To achieve the first capability, the pump 48 is selected and configured so as to be operable in a prolonged priming mode to generate a suction or partial vacuum condition in the enclosed liquid path 46 to draw the liquid personal hygiene product from the reservoir 40 to fill the enclosed liquid path 46. This can also encompass filling all or part of the dispensing portion 52 or conduit extending from the pump 48 to the dispensing outlet 26. The pump 48 also is configured to have a standby mode that maintains a sufficient portion of the suction or partial vacuum condition to hold the liquid personal hygiene product in the enclosed liquid path 46, and the dispensing portion 52 or conduit, if that portion is to contain product. In this latter regard, this may be deemed further advantageous as product will be present immediately adjacent to the dispensing outlet 26 so that when the pump 48 is subsequently actuated to dispense product, a quantity of the product will be more quickly or immediately dispensed from the dispensing outlet 26. Further in this regard, the dispensing portion 52 of the path 46 preferably advantageously has a capacity (internal volume) to hold one or more multiples of a discrete quantity of the product desired to be dispensed onto each hand, e.g., typically a fraction of an ounce (if the product is foamed so as to expand when dispensed to atmosphere, the quantity in the liquid state will be smaller and the foamed quantity greater). The overall enclosed liquid path 46 preferably has an internal volume equal to several multiples of the desired discrete quantity of the product, to be able to dispense a large number of discrete quantities of the product in rapid succession.

As a pump 48, a peristaltic pump is preferred, as it can be selected and constructed to have a self-priming capacity that allows the reservoir 40 to be located well below the pump 48, and such that a relatively long enclosed liquid path 46 can be used to connect the two but importantly also hold a significant quantity of hygiene product awaiting dispensing. This is in part achieved by pinching closed the portion of the enclosed path 46, e.g., rubber or plastic tube, by one or more lobes, rollers, or vanes of the peristaltic pump 48 when the pump 48 is not operating. The peristaltic pump 48 thus acts as a mechanical check valve to prevent back flow of the liquid product when the pump 48 is not actively pumping. The pinched closed condition also prevents back flow of vapor or gas through the pump 48, which back flow would be required to replace the liquid product in the upper region of the enclosed path 46 on the upstream or supply side of the peristaltic pump 48 were the liquid product have a tendency to begin to drain back toward the reservoir when the pump is not operating. In this regard, if a low vapor pressure liquid product were to be selected for use under conditions where vaporization of the product within the enclosed path was to be expected, an additional mechanical check valve could be employed between the pump and the reservoir to prevent the back flow. Contributing to the maintaining of the liquid product in the enclosed liquid path 46 between the reservoir 40 and pump 48, will be residual partial vacuum within the path, which will be trapped by the pinched state of the tube within the pump 48 when not operating, e.g., in the standby state or between dispensing individual quantities of the product, and possibly viscous friction between the liquid product and the walls of the tubing of the enclosed path, and capillarity. The pinched state of the enclosed path 46 and other conditions holding the liquid stationary will have the same effect on the liquid in the enclosed liquid path 46 between the pump and the dispensing outlet, and as an additional feature a P-type trap can be employed in that portion of the path 46. An advantage found is that, as a result, a relatively low power pump can be used and will dispense product virtually upon activation. So with the peristaltic pump 48 desirably constructed such that the lobes or rollers thereof tightly pinch a tubular section carrying the liquid product closed to create a sealed condition between the inlet and outlet or discharge ends thereof when not operating, to hold the liquid product within the lengthy vertical enclosed liquid passage and optionally the dispensing end with the pump in standby, subsequent initiation of operation of the pump 48 from this state will result in immediate pumping of product from the pump 48 toward the dispensing outlet. As a non-limiting example, a peristaltic pump 48 having about a 1-2 inch diameter 3 lobe or roller impeller has been found to dispense a suitable discrete quantity of liquid product for hand sanitizing with a single revolution or less of pump operation.

According to another aspect of the invention, an electrically powered control device 56 is connected in control of the pump 48, e.g., via a wiring harness or the like, and to a power source 58, which can be, as a non-limiting example, a battery pack carried on or in the housing, or a standard electrical outlet. The control device 56 can optionally additionally connect to one or more additional pumps 48 as shown, or each pump 48 can have its own control device 56. Thus, for example, as shown with 2 pumps 48, 2 control devices 56 can be employed, and for 4 pumps 48, 4 control devices 56 can be employed. The control device 56 can be a processor operated device connected to a memory, or a simpler analogue device, in either event, it is operable responsive to an input, which can be, for example a manual switch, graphic user interface, timer, or the like, to power and operate the pump 48 in the prolonged mode to fill the enclosed liquid path 46 with product. The duration of the prolonged mode can be determined by activation of the switch, timer setting, or a programmed function if a digital processor and memory is employed.

Addressing plumbing of multiple pumps 48, for ease of modularity, it is contemplated that each pump 48 is individually plumbed to a common manifold 60 (FIGS. 7 and 8) in connection with the reservoir 40 via branches of liquid path 46 from which the liquid product will be drawn. However, as an alternative, the pumps 48 can be individually plumbed between the reservoir 40 and their respective dispensing outlet 26. As still another alternative, a single pump 48 operable to maintain a pressure head of the liquid product, in connection with the multiple dispensing outlets 26 via individual valves could be used.

The control device 56 includes or interfaces or connects, e.g., via wires of a wiring harness, or a wireless or network connection, to a touchless sensor circuit 62. The sensor circuit 62 includes a sensor 64 which can be of conventional construction and operation automatically operable in a sensing mode to sense presence of a person's hand 22, and responsively output a signal or power to the control device 56 to actuate the pump 48 in a controlled momentary operating mode for dispensing the discrete quantity of product. As a preferred configuration and operation, the sensor 64 will periodically emit a signal within a predetermined elongate sensing region 66 (FIG. 8) external to the sensor 64, that will be reflected back to the sensor 64 by a person's hand 22 when present in the sensing region 66. The control device 56 or the sensor circuit 62 can incorporate a timer, voltage regulator, potentiometer, or similar device, or can be programmed, to limit operation of the pump 48 to the desired momentary period, which can be optionally adjustable. The sensor 64 can similarly have one sampling rate, or a variable sampling rate, wherein the signal is emitted only periodically, e.g., two or more times a second, to save energy when there is little activity, and which rate increases when a hand or hands is/are initially sensed. The pump 48 can also be variable in operation, such as by being DC powered, and by regulating the voltage level, e.g., 12 volts DC plus or minus some number of volts.

The sensor 64 is preferably located remotely of the control device 56, in or on a dispensing spout 68, in association with the dispensing outlet 26. The sensor 64 is preferably positioned and configured such that the sensing region 66 is closely parallel to or coextensive with the associated elongate dispensing path 24 along which the liquid product will flow when dispensed. The sensor circuit 62 is automatically operable responsive to the sensed presence of a person's hand within the predetermined elongate sensing region to activate the pump 48 from its standby mode, momentarily to dispense the discrete quantity of the liquid personal hygiene product from the dispensing outlet 26 along the dispensing path 24, then allow the pump 48 to deactivate and return to the standby mode. This can be programmed, or analogue controlled using a timer.

Figure 8A:
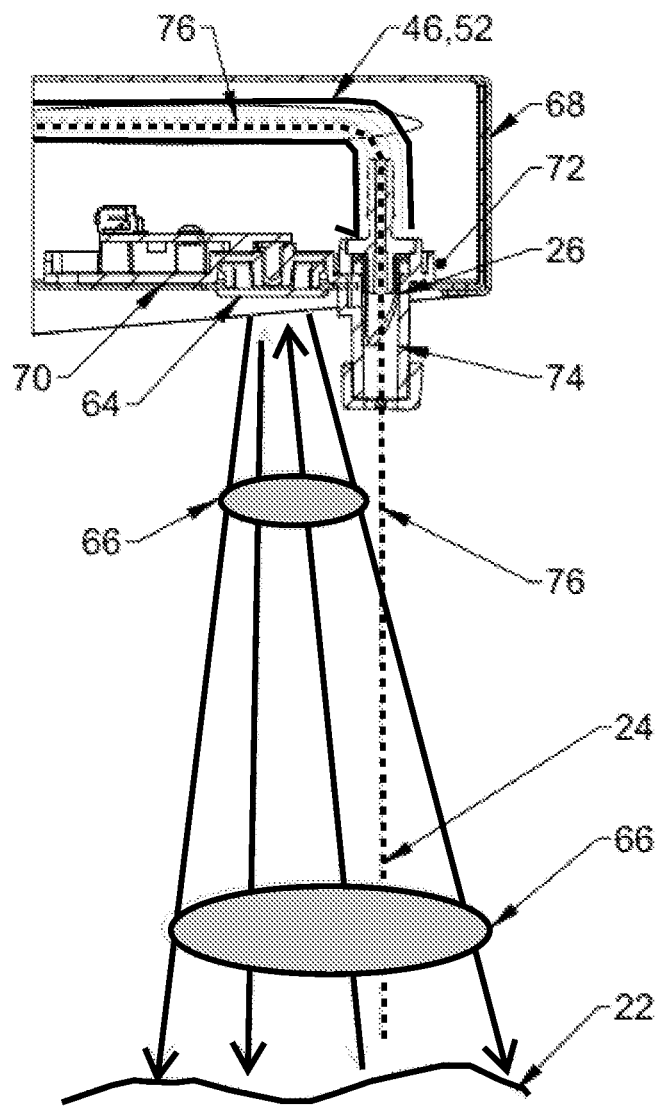
FIG. 8A is a simplified diagrammatic view of a dispensing station of the apparatus, illustrating dispensing of product from a dispensing outlet within a dispensing spout and a relationship thereof with a hand sensing region.
Figure 9:
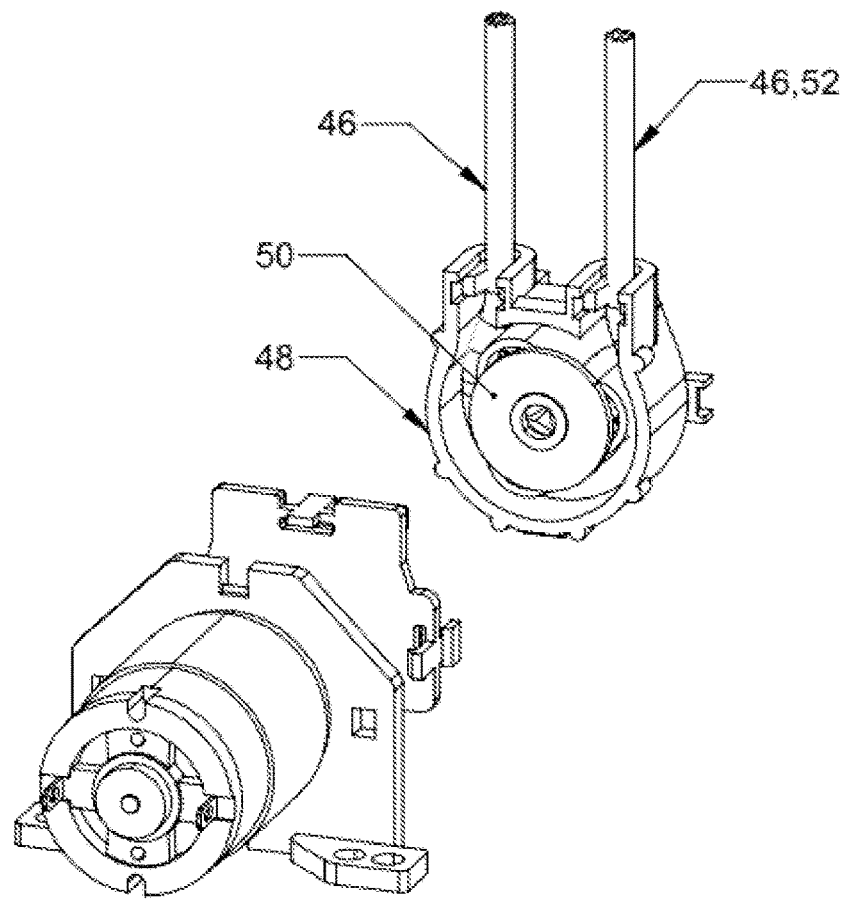
FIG. 9 shows a representative peristaltic pump used in the invention, and illustrating a continuous section of tubing extending through the pump is part of the enclosed liquid path, carrying product to be dispensed.
Figure 10:
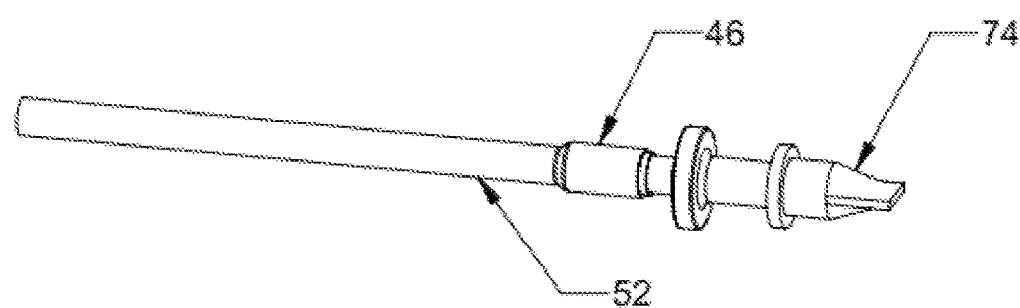
FIG. 10 shows a dispensing portion of the enclosed liquid path, and an associated duckbill valve thereon.

As a suitable sensor 64, a laser, infrared, radio, or ultrasonic signal emitter/receiver can be used as suitable for a particular application, it being desirable for the sensor 64 to have the capability to sense a hand 22 or hands within a sensing region 66 of several inches in length but having a relatively narrow width similar in width to or just smaller than, a representative hand span. The sensor 64 is preferably mounted so that the elongate sensing region 66 is coincident with or contains the dispensing path 24 of the dispensing outlet 26, see FIG. 8A, so that a hand 22 when sensed will be in the dispensing path 24. To accomplish this, the sensor 64 and associated circuit 62 is preferably located on a circuit board 70 (FIG. 5 also) that is mounted on or in the dispensing spout 68 in relation to the dispensing outlet 26 so as to be closely aligned with the dispensing path 24. More particularly, the circuit board 70 will be mounted so that the sensor 64 faces down to position and orient the elongate sensing region 66 is coincident with or ensconces the dispensing path 24 such that the sensor 64 will sense the presence of a hand 22 or part of a hand when in the dispensing path 24, including when spaced a hand span or more below the dispensing outlet 26 within the sensing region 66. The dispensing outlet 26 can be retained on or jointly with, the circuit board 70, and can pass through an opening 72 therein adjacent to the sensor 64 to achieve desired coincidence of the dispensing path 24 and the sensing region 66.

As a preferred embodiment, sensor 64, will comprise a laser sensor having an emitter that emits a downward laser signal along a sensing region closely parallel to or coincident with the elongate downward extending dispensing path 24, along substantially the length thereof, such that a hand that enters the dispensing path 24 anywhere along the length thereof, including a hand span or more below dispensing outlet 26, will be sensed to initiate dispensing of the personal hygiene product along the dispensing path with a high likelihood of landing on the hand. An advantage of a laser signal include that it can have a focused beam that is similar in sectional extent to that of the dispensing path so as to be essentially coincident or closely beside the dispensing path, such that a hand must be correspondingly close or within the dispensing path to be sensed. Another advantage is that the laser sensor can have a tuned frequency range that allows the sensor to discriminate the reflected laser light from ambient light, e.g, indoor lighting and natural lighting including bright sunlight, as well as other directed lights, e.g., LED emitted light, that may be present. Another advantage is that the signal can be narrowly focused and thus not dispersed so that a hand will necessarily have to be very close to the dispensing path to be sensed. In this regard, the dispensing path is contemplated to be relatively narrow laterally and the sensing region will have a similarly narrower lateral extent, but be directly next to or beside the dispensing path, or be coincident with the dispensing path, to provide reasonable likelihood of sensing hands only within the dispensing path. Further in this regard, it is contemplated that a sensor employed can have 2 or more laser sensing elements or tubes that allow sensing direction of hand motion and the sensor circuitry would be operable to determine whether a hand is moving into the dispensing path or out of it, or both, in a back and forth or waving action, and thusly determine whether to dispense or not. This would apply to other types of sensors, including but not limited to infrared sensors, also.

Further in regard to the dispensing stations 28, it is desirable in terms of adaptability for various applications to have the capability to increase or decrease the number of dispensing stations, as well as their location and/or height. To provide this capability, the external surfaces of housing 38 can have alternative mounting locations for dispensing spouts 68 and catch basins 54, and openings for passage of dispensing portions 52 of the enclosed liquid path 46 and wiring to the touchless sensor circuits 62. This can comprise, for instance, keyhole openings having removable cover panels to allow installing spouts 68 and catch basins 54, using machine or sheet metal screws or the like. The use of flexible tubing for the liquid path and wiring harnesses or wireless connections with the touchless sensor circuit provide easy modularity, and the panels that hold the control devices and pumps allow snap in or similar installation to enable quickly and easily configuring the apparatus and moving stations as desired.

The dispensing outlet 26 can include a valve 74 (FIGS. 8A, 10) having a normally closed state and is openable by application of pressure generated by the pump against the liquid personal hygiene product 76 when located in the dispensing portion 52, to dispense the discrete quantity of the product 76 in a narrower stream in at least one lateral dimension, e.g., a fan, and also to help contain the product 76 within portion 52 until dispensed. A rubbery duckbill valve 74 fitted to the end of flexible tubing used as portion 52 has been found to work well and can be oriented to best fit the dispensing line to the sensing region. As another advantage, a valve such as duckbill valve 74 will reduce evaporation of product 76 within dispensing portion 52 during long standby periods or storage.

According to another preferred aspect, when the pump 48 is momentarily actuated to dispense the liquid product, at the same time a partial vacuum condition is created in the enclosed liquid path 46 sufficient to draw an amount of product from the reservoir 40 about equal to the discrete quantity of the liquid personal hygiene product dispensed, so that the liquid path 46 remains full and ready to dispense in rapid succession.

In light of all the foregoing, it should thus be apparent to those skilled in the art that there has been shown and described a RAPID TOUCHLESS AUTOMATIC DISPENSING STATION APPARATUS, SYSTEM, AND METHOD according to the invention. However, it should also be apparent that, within the principles and scope of the invention, many changes are possible and contemplated, including in the details, materials, and arrangements of parts which have been described and illustrated to explain the nature of the invention. Thus, while the foregoing description and discussion addresses certain preferred embodiments or elements of the invention, it should further be understood that concepts of the invention, as based upon the foregoing description and discussion, may be readily incorporated into or employed in other embodiments and constructions without departing from the scope of the invention. Accordingly, the following claims are intended to protect the invention broadly as well as in the specific form shown, and all changes, modifications, variations, and other uses and applications which do not depart from the spirit and scope of the invention are deemed to be covered by the invention, which is limited only by the claims which follow.

What is claimed is:

1. A touchless automatic liquid product dispensing station apparatus, comprising:
a housing carrying:
a reservoir disposed in the housing, having an interior cavity for receiving and holding a first quantity of the liquid product;
an enclosed liquid path extending upward from the interior cavity of the reservoir to a pump disposed above the reservoir, the enclosed liquid path comprising a manifold having a manifold chamber for holding a quantity of the liquid product equal to several multiples of the discrete quantity of the liquid product, disposed between the reservoir and the pump, the pump being controllably operable in a prolonged priming mode to create a partial vacuum condition within the enclosed fluid path to draw the liquid product from the interior cavity of the reservoir up through the enclosed liquid path into the pump, the pump having an inactive standby mode to pinch closed the enclosed liquid path sufficient to hold the liquid product therein, and the pump being controllably operable from the standby mode in a momentary dispensing mode multiple times shorter than the prolonged priming mode to dispense a discrete quantity of the liquid product while creating a partial vacuum condition in the enclosed liquid path sufficient to draw more of the liquid product from the reservoir into the enclosed liquid path to replace the dispensed liquid product;
an elongate enclosed dispensing conduit extending from the pump through a dispensing spout attached to the housing, to a dispensing outlet located external to the housing from which the discrete quantity of the liquid product is dispensed to flow down along a predetermined elongate open dispensing path externally of the dispensing conduit and the dispensing spout;
an electrically powered control device connected in operative control of the pump, comprising:

an input operable activate the pump to operate in the prolonged priming mode to fill the enclosed liquid path and optionally all or part of the enclosed dispensing conduit with the liquid product, and thereafter deactivate the pump to the standby mode;

a touchless input device including a circuit board, a sensor having an on state to sense presence of a person's hand along a predetermined elongate sensing region external to the sensor when the pump is in the standby mode, and circuitry on the circuit board automatically operable to immediately initiate operation of the pump from the standby mode in the momentary dispensing mode responsive to the sensed presence of a hand in the elongate sensing region, then automatically return the pump to the standby mode, or again initiate operation of the pump in the momentary dispensing mode responsive to the sensed presence of another hand in the sensing region, the circuit board being located in or on the dispensing spout to position the sensor in predetermined relation to the dispensing conduit such that the sensor faces down to position and orient the elongate sensing region coincident with the dispensing path such that the sensor will sense the presence of a hand when in the dispensing path, including when spaced a hand span or more below the dispensing outlet within the sensing region.

2. The dispensing station apparatus of claim 1, wherein the enclosed liquid path comprises a second section extending from the manifold to a second pump disposed above the reservoir, the second pump being controllably operable in a prolonged priming mode to create a partial vacuum condition within the second section to draw the liquid product therethrough from at least the manifold into the second pump, the second pump having an inactive standby mode to pinch the second section to hold the liquid product therein, and the second pump being controllably operable from the standby mode thereof in a momentary dispensing mode thereof multiple times shorter than the prolonged priming mode to dispense a discrete quantity of the liquid product while creating a partial vacuum condition in the second section sufficient to draw more of the liquid product from the manifold into the second section to replace the liquid product dispensed by the second pump;

a second elongate enclosed dispensing conduit extending from the second pump through a second dispensing spout attached to the housing, to a second dispensing outlet located external to the housing from which the discrete quantity of the liquid product is dispensed by the second pump to flow down along a second predetermined elongate open dispensing path externally of the second dispensing conduit and the second dispensing spout;

a second electrically powered control device connected in operative control of the second pump, comprising:

a second input operable activate the second pump to operate in the prolonged priming mode thereof to fill the second section of the enclosed liquid path and optionally all or part of the second enclosed dispensing conduit with the liquid product, and thereafter deactivate the second pump to the standby mode thereof;

a second touchless input device including a second circuit board, a second sensor having an on state to sense presence of a person's hand along a second predetermined elongate sensing region external to the second sensor when the second pump is in the standby mode thereof, and circuitry on the second circuit board automatically operable to immediately initiate operation of the second pump from the standby mode thereof in the momentary dispensing mode thereof responsive to the sensed presence of a hand in the second elongate sensing region, then automatically return the second pump to the standby mode thereof, or again initiate operation of the second pump in the momentary dispensing mode thereof responsive to the sensed presence of another hand in the second sensing region, the second circuit board being located in or on the second dispensing spout to position the second sensor in predetermined relation to the second dispensing conduit such that the second sensor faces down to position and orient the second elongate sensing region coincident with the second dispensing path such that the second sensor will sense the presence of a hand when in the second dispensing path, including when spaced a hand span or more below the second dispensing outlet within the second sensing region.

3. The dispensing station apparatus of claim 2, wherein at least the second dispensing spout is removably attached to the housing at a selected one of at least two locations on the housing.

4. The dispensing station apparatus of claim 2, wherein the dispensing spout and the second dispensing spout are attached to the housing at different heights.

5. The dispensing station apparatus of claim 2, wherein the dispensing spout and the second dispensing spout are attached to different sides of the housing.

6. The dispensing station apparatus of claim 1, wherein the circuitry of the touchless input device is automatically operable to repeatedly initiate operation of the pump in the momentary dispensing mode responsive to sensed presence of a succession of hands along the elongate sensing region, respectively.

7. The dispensing station apparatus of claim 1, wherein the circuitry of the touchless input device includes a device adjustable to set a duration of the operation of the pump in the momentary dispensing mode to adjust a volume of the discrete quantity of the liquid product.

8. The dispensing station apparatus of claim 1, wherein the electrically powered control device comprises a device adjustable to set a duration of the operation of the pump in the momentary dispensing mode to enable adjusting a volume of the discrete quantity of the liquid product.

9. The dispensing station apparatus of claim 8, wherein the pump comprises a peristaltic pump, and the device adjustable to set the duration of the operation of the pump comprises a timer, a voltage regulator, or a potentiometer.

10. The dispensing station apparatus of claim 1, wherein the dispensing outlet of the elongate enclosed dispensing conduit includes a valve having a normally closed state and is openable by application of pressure generated by the pump against the discrete quantity of the liquid product located in the elongate enclosed dispensing conduit, to dispense the discrete quantity of the liquid product so as to converge with the sensing region along the length thereof.

11. The dispensing station apparatus of claim 1, wherein the pump in the standby mode will create a partial vacuum condition in the enclosed dispensing conduit sufficient in combination with the pinching of the path to hold any of the liquid product present therein until initiation of the operation of the pump in the momentary dispensing mode.

12. The dispensing station apparatus of claim 1, wherein the enclosed liquid path comprises a check valve that operates to prevent flow of the liquid product backward toward the reservoir.

13. The dispensing station apparatus of claim 1, wherein the liquid product comprises a gel.

14. The dispensing station apparatus of claim 1, wherein the liquid product comprises a sanitizer.

15. The dispensing station apparatus of claim 1, wherein the housing is telescopically adjustable in height.

16. The dispensing station apparatus of claim 1, wherein the sensor operable to sense presence of a person's hand along the predetermined elongate sensing region external to the sensor dispensing spout comprises a signal emitter that emits a narrow light signal alongside the dispensing path that is reflected by a person's hand or portion thereof, back to the sensor.

17. The dispensing station apparatus of claim 1, wherein the housing is modular and comprises mounting structure for a plurality of the pumps therein, a plurality of the dispensing spouts at different locations thereon, and a plurality of the control devices therein.

18. The dispensing station apparatus of claim 1, wherein the pump comprises a peristaltic pump, and the enclosed liquid path comprises a continuous tube extending therethrough.

19. A touchless automatic liquid product dispensing station apparatus, comprising:
a housing carrying:
a reservoir disposed in the housing, having an interior cavity for receiving and holding a first quantity of the liquid product;
an enclosed liquid path extending upward from the interior cavity of the reservoir to a pump disposed above the reservoir, the pump being controllably operable in a prolonged priming mode to create a partial vacuum condition within the enclosed fluid path to draw the liquid product from the interior cavity of the reservoir up through the enclosed liquid path into the pump, the pump having an inactive standby mode to pinch closed the enclosed liquid path sufficient to hold the liquid product therein, and the pump being controllably operable from the standby mode in a momentary dispensing mode multiple times shorter than the prolonged priming mode to dispense a discrete quantity of the liquid product while creating a partial vacuum condition in the enclosed liquid path sufficient to draw more of the liquid product from the reservoir into the enclosed liquid path to replace the dispensed liquid product;
an elongate enclosed dispensing conduit extending from the pump through a dispensing spout attached to the housing, to a dispensing outlet located external to the housing from which the discrete quantity of the liquid product is dispensed to flow down along a predetermined elongate open dispensing path externally of the dispensing conduit and the dispensing spout;
an electrically powered control device connected in operative control of the pump, comprising:
an input operable activate the pump to operate in the prolonged priming mode to fill the enclosed liquid path and optionally all or part of the enclosed dispensing conduit with the liquid product, and thereafter deactivate the pump to the standby mode;
a touchless input device including a circuit board, a sensor having an on state to sense presence of a person's hand along a predetermined elongate sensing region external to the sensor when the pump is in the standby mode, and circuitry on the circuit board automatically operable to immediately initiate operation of the pump from the standby mode in the momentary dispensing mode responsive to the sensed presence of a hand in the elongate sensing region, then automatically return the pump to the standby mode, or again initiate operation of the pump in the momentary dispensing mode responsive to the sensed presence of another hand in the sensing region, the circuit board being located in or on the dispensing spout to position the sensor in predetermined relation to the dispensing conduit such that the sensor faces down to position and orient the elongate sensing region coincident with the dispensing path such that the sensor will sense the presence of a hand when in the dispensing path, including when spaced a hand span or more below the dispensing outlet within the sensing region; and
a device adjustable to set a duration of the operation of the pump in the momentary dispensing mode to adjust a volume of the discrete quantity of the liquid product.

20. A touchless automatic liquid product dispensing station apparatus, comprising:
an adjustable height housing carrying:
a reservoir disposed in the housing, having an interior cavity for receiving and holding a first quantity of the liquid product;
an enclosed liquid path extending upward from the interior cavity of the reservoir to a pump disposed above the reservoir, the pump being controllably operable in a prolonged priming mode to create a partial vacuum condition within the enclosed fluid path to draw the liquid product from the interior cavity of the reservoir up through the enclosed liquid path into the pump, the pump having an inactive standby mode to pinch closed the enclosed liquid path sufficient to hold the liquid product therein, and the pump being controllably operable from the standby mode in a momentary dispensing mode multiple times shorter than the prolonged priming mode to dispense a discrete quantity of the liquid product while creating a partial vacuum condition in the enclosed liquid path sufficient to draw more of the liquid product from the reservoir into the enclosed liquid path to replace the dispensed liquid product;
an elongate enclosed dispensing conduit extending from the pump through a dispensing spout attached to the housing, to a dispensing outlet located external to the housing from which the discrete quantity of the liquid product is dispensed to flow down along a predetermined elongate open dispensing path externally of the dispensing conduit and the dispensing spout;
an electrically powered control device connected in operative control of the pump, comprising:
an input operable activate the pump to operate in the prolonged priming mode to fill the enclosed liquid path and optionally all or part of the enclosed dispensing conduit with the liquid product, and thereafter deactivate the pump to the standby mode;
a touchless input device including a circuit board, a sensor having an on state to sense presence of a person's hand along a predetermined elongate sensing region external to the sensor when the pump is in the standby mode, and circuitry on the circuit board automatically operable to immediately initiate operation of the pump from the standby mode in the momentary dispensing mode responsive to the sensed presence of a hand in the elongate sensing region, then automatically return the pump to the standby mode, or again initiate operation of the pump in the momentary dispensing mode responsive to the sensed presence of another hand in the sensing region, the circuit board being located in or on the dispensing spout to position the sensor in predetermined relation to the dispensing conduit such that the sensor faces down to position and orient the elongate sensing region coincident with the dispensing path such that the sensor will sense the presence of a hand when in the dispensing path, including when spaced a hand span or more below the dispensing outlet within the sensing region.

* * * * *